(12) United States Patent
Lee et al.

(10) Patent No.: US 10,908,162 B2
(45) Date of Patent: Feb. 2, 2021

(54) METHODS RELATED TO VOLATILE COMPOUNDS IN GENITOURINARY CANCERS

(71) Applicants: Wen-Yee Lee, El Paso, TX (US); Qin Gao, El Paso, TX (US); Xiaogang Su, El Paso, TX (US)

(72) Inventors: Wen-Yee Lee, El Paso, TX (US); Qin Gao, El Paso, TX (US); Xiaogang Su, El Paso, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 6 days.

(21) Appl. No.: 16/170,553

(22) Filed: Oct. 25, 2018

(65) Prior Publication Data

US 2019/0128890 A1 May 2, 2019

Related U.S. Application Data

(60) Provisional application No. 62/577,983, filed on Oct. 27, 2017.

(51) Int. Cl.
*G01N 33/574* (2006.01)

(52) U.S. Cl.
CPC . *G01N 33/57434* (2013.01); *G01N 33/57438* (2013.01); *G01N 2560/00* (2013.01)

(58) Field of Classification Search
None
See application file for complete search history.

(56) References Cited

U.S. PATENT DOCUMENTS

| | | | | |
|---|---|---|---|---|
| 2012/0126111 A1* | 5/2012 | Chaubron | ........ | G01N 33/57407 250/282 |
| 2012/0326092 A1* | 12/2012 | Haick | .............. | G01N 33/57415 252/408.1 |
| 2019/0079092 A1* | 3/2019 | Boyden | .................. | G01N 30/72 |

FOREIGN PATENT DOCUMENTS

WO WO-2015161078 A1 * 10/2015 ........... G01N 33/574

OTHER PUBLICATIONS

Schmidt et al., J Biomark, Mar. 30, 2015 (Year: 2015).*
Bax et al. Cancers, 2018, 10, 123, p. 1-29 (Year: 2018).*
Nunzio et al. Urologic Oncology, Seminars and Original Investigations 32, 2014, 35.e9-35.e13 (Year: 2014).*
Carneiro,Tumor Biology, Sep. 2018, 1-12). (Year: 2018).*
Diamandis, BMC Medicine, 2012, 10, 87, p. 1-5 (Year: 2012).*
Alford, Rev Urol 2017, 19(4):221-234 (Year: 2017).*
O'connor, Nature, Mar. 14, 2017 (Year: 2017).*
Smith et al. (IEEE Sensors J, Jan. 10, 2010) (Year: 2010).*

Ashley, et al., "Determining Volatile Organic Compounds in Human Blood from a Large Sample Population by Using Purge and Trap Gas Chromatography/Mass Spectrometry," *Analytical Chemistry*, 64(9) 1021-29, 1992.
Balseiro and Correia, "Is Olfactory Detection of Humans Cancer by Dogs Based on Major Histocompatibility Complex-Dependent Odour Components?—A Possible Cure and a Precocious Diagnosis of Cancer," *Medical Hypotheses*, 66(2);270-72, 2006.
Bax, et al., "Innovative Diagnostic Methods for Early Prostate Cancer Detection Through Urine Analysis: A Review," *Cancers*, 10(123); 1-29, 2018.
Bjartell, "Dogs Sniffing Urine: A Future Diagnostic Tool or a Way to Identify New Prostate Cancer Markers," *European Urology*, 59(2); 202-203, 2011.
Boedeker, et al., "Sniffer Dogs as Part of a Bimodal Bionic Research Approach to Develop a Lung Cancer Screening," *Interactive Cardiovascular and Thoracic Surgery*, 14(5); 511-515, 2012.
Buszewski, et al., "Analytical and Unconventional Methods of Cancer Detection Using Odor," *Trends in Analytical Chemistry*, 38; 1-12, 2012.
Capelli, et al., "Application and Uses of Electronic Noses for Clinical Diagnosis on Urine Samples: A Review," *Sensors*, 16(1708); 1-23, 2016.
Cooperberg, et al., "The University of California, San Francisco Cancer of the Prostate Risk Assessment Score: A Straightforward and Reliable Preoperative Predictor of Disease Recurrence After Radical Prostatectomy," *Journal of Urology*, 173(6); 1938-1942, 2005.
Cornu, et al., "Olfactory Detection of Prostate Cancer by Dogs Sniffing Urine: A Step Forward in Early Diagnosis," *European Urology*, 59(2); 197-201, 2011.
De Lacy Costello, et al., "Volatile Organic Compounds (VOCs) Found in Urine and Stool," *Volatile Biomarkers: Non Invasive Diagnosis in Physiology and Medicine*, 1$^{st}$ Elsevier, Chapter 22; 405-462, 2013.
Di Lena, et al., "Volatile Organic Compounds as New Biomarkers for Colorectal Cancer: A Review," *Colorectal Disease*, 18(7); 654-663, 2016.
Filipiak, et al., "TD-GC-MS Analysis of Volatile Metabolites of Human Lung Cancer and Normal Cells In Vitro," *Cancer Epidemiology, and Prevention*, 19(1); 182-95, 2010.
Gallagher et al., "Analyses of Volatile Organic Compounds from Human Skin," *British Journal of Dermatology*, 159(4); 780-91, 2008.
Gao, et al., "Application of Urinary Volatile Organic Compounds (VOCs) for the Diagnosis of Prostate Cancer," *Clinical Genitourinary Cancer*; 1-9, 2019.
Jimenez-Pacheco, et al., "Furan and P-Xylene as a Candidate Biomarkers for Prostate Cancer," *Urologic Oncology: Seminars and Original Investigations*, 3; 243e21-243e27, 2018.

(Continued)

*Primary Examiner* — Umamaheswari Ramachandran
(74) *Attorney, Agent, or Firm* — Norton Rose Fulbright US LLP

(57) ABSTRACT

Embodiments are directed to methods of identifying a subject having prostate cancer or renal cell carcinoma; or prostate cancer risk assessment of a subject by determining level of at least one volatile organic compound from a sample from the subject where a significantly different level of the at least one volatile organic compound in the sample as compared to the level of the compound in a control sample is indicative of the presence of prostate cancer or renal cell carcinoma or low-risk prostate cancer or high-low prostate cancer in the subject.

6 Claims, 12 Drawing Sheets

(56) References Cited

OTHER PUBLICATIONS

Khalid, et al, "Urinary Volatile Organic Compounds for the Detection of Prostate Cancer," *PLoS One*, 10(11); e0143283, 2015.

Li, et al., "Investigation of Potential Breath Biomarkers for the Early Diagnosis of Breast Cancer Using Gas Chromatography-Mass Spectrometry," *Clinica Chimica Acta*, 436; 59-67, 2014.

Nakhleh, et al., "Diagnosis and Classification of 17 Diseases from 1404 Subjects via Pattern Analysis of Exhaled Molecules," *ACS Nano*, 11(1); 112-125, 2016.

Nissinen, et al., "Detection of Pancreatic Cancer by Urine Volatile Organic Compound Analysis," *AntiCancer Research*, 39; 73-79, 2019.

Peng, et al., "Diagnosing Lung Cancer in Exhaled Breath Using Gold Nanoparticles," *Nature Nanotechnology*, 4; 669-73, 2009.

Phillips, et al., "Variation in Volatile Organic Compounds in the Breath of Normal Humans," *Journal of Chromatography B: Biomedical Sciences and Applications*, 729(1-2); 75-88, 1999.

Pirrone & Albertini, "Olfactory Detection of Cancer by Trained Sniffer Dogs: A Systematic Review of the Literature," *Journal of Veterinary Behavior*, 19; 105-117, 2017.

Song, et al., "Quantitative Breath Analysis of Volatile Organic Compounds of Lung Cancer Patients," *Lung Cancer*, 67; 227-231, 2010.

Tavern, et al., "Olfactory System of Highly Trained Dogs Detects Prostate Cancer in Urine Samples," *The Journal of Urology*, 193(4); 1382-1387, 2015.

Thompson, et al., "Assessing Prostate Cancer Risk: Results from the Prostate Cancer Prevention Trial," *Journal of the National Cancer Institute*, 98(8); 529-534, 2006.

Thriumani, et al., "A Study on VOCs Released by Lung Cancer Cell Line Using GCMS-SPME," *Procedia Chemistry*, 20; 1-7, 2016.

Tong, et al., "Volatile Organic Metabolites Identify Patients with Gastric Carcinoma, Gastric Ulcer, or Gastritis and Control Patients," *Cancer Cell International*, 17; 1-9, 2017.

Willis, et al., "Volatile Organic Compounds as Biomarkers of Bladder Cancer: Sensitivity and Specificity Using Trained Sniffer Dogs," *Cancer Biomarkers*, 8(3); 145-53, 2011.

Zhou, et al., "Review of Recent Developments in Determining Volatile Organic Compounds in Exhaled Breath as Biomarkers for Lung Cancer Diagnosis," *Analytical Chimica Acta*, 996; 1-9, 2017.

\* cited by examiner

Benzimidazole, 2-benzylsulfonyl-

Bicyclo[4.2.0]octa-1,3,5-triene

Decanamide, N-(2-hydroxyethyl)-

N-Methyltaurine

METHODS RELATED TO VOLATILE COMPOUNDS IN GENITOURINARY CANCERS

CROSS REFERENCE TO RELATED APPLICATIONS

This application claims priority to U.S. Provisional Patent application Ser. No. 62/577,983 filed Oct. 27, 2017, which is incorporated herein by reference in its entirety.

STATEMENT REGARDING FEDERALLY FUNDED RESEARCH

None.

BACKGROUND OF THE INVENTION

A. Field of the Invention

The invention generally concerns a methods diagnosing or prognosing genitourinary cancers. In particular the methods include detecting and assessing levels of volatile organic compounds associated with prostate and renal cancer.

B. Background

Cancer is a leading cause of death and disability globally, impacting more than 14 million people each year.[1] In United States, prostate cancer (PCa) is the second most common cancer and the second leading cause of death in men. In 2017, about 161,360 new cases of PCa and about 26,730 deaths in PCa are estimated in United States according to the American Cancer Society. About 1 in 7 men will be diagnosed with PCa during his lifetime.[2] As early diagnosis and treatment of PCa will improve the quality of care and reduce mortality, there is a high demand of reliable, quick and patient-friendly diagnostic method for PCa screening. Clinical researchers increasingly recognize the importance of risk stratification of PCa and the risk-adapted treatment strategies[92,93]. Different risk factors associated with PCa have been integrated into individualized risk prediction, including PSA, Gleason score, T stage, and other risk factors[94,95]. Again, the abovementioned risk-assessment factors require invasive procedure and the accuracy of PSA is questionable. Therefore, there is a significant interest in finding a more sensitive, reliable and cost effective PCa screening and prognosis biomarkers.

Nowadays, most prostate cancers are screened by a prostate-specific antigen (PSA) blood test or a digital rectal exam (DRE). If the PCa is suspected based on the results of screening tests or other symptoms, further tests, including trans-rectal ultrasound (TRUS) and prostate biopsy will be required to confirm the diagnosis.[3] When the PCa develops, the PSA level usually goes above 4 ng/mL. Still, a level below 4 does not guarantee that a man doesn't have cancer. About 15% of men with a PSA below 4 will have PCa on a biopsy.[3] In addition, in the late 1990s, scientists have reported that the possibility of having PCa at 2.5-4.0 ng/ml PSA levels was similar to that with 4-10 ng/ml.[4,5] Although PSA has been widely used as a useful tool for PCa screening, PSA is not cancer-specific.[6] As a result, the low specificity is not sufficient to make PSA a reliable tumor marker for early detection of PCa.[6]

Kidney cancer accounts for more than 2% of cancer incidence and mortality in the United States, which would include nearly 65,340 new cases (3.8%) and 14,970 deaths estimated for 2018.[86] The most common type of kidney cancer is renal cell carcinoma (RCC), about 9 RCC out of 10 kidney cancers. RCC is a heterogeneous malignancy, both morphologically and genetically, which is classified into different histologic subtypes, including clear cell RCC (most common one), papillary RCC, chromophobe RCC, oncocytoma RCC and other less common subtypes.[87-89] The outcome of RCC is usually unpredictable even after a long period of asymptomatically development and progression.[90] Therefore, its diagnosis is often incidental through the use of medical imaging and it is frequently at an advanced stage and metastatic when detected clinically.[91] However, no early screening method is recommended to screen for kidney cancer in people at average risk or increasing risk.

Furthermore, techniques used in advanced stages, such as bone scans, computed tomography (CT) scan, and magnetic resonance imaging (MRI), may involve x rays, magnetic fields, sound waves and radioactive substances which can lead to a second injury of cancer patients.[3] Diagnostic methods to reduce stress and detrimental effects in patients are needed.

There remains a need for PCa and RCC diagnostic and prognosis methods with high sensitivity and high specificity.

SUMMARY OF THE INVENTION

Volatile organic compounds (VOCs) are continuously generated from the human body and released through breath, blood, skin, urine and fecal samples.[7-10] It stands to reason that in some way these VOCs carry information on the physiological and metabolic status of the individual.[11] Thus, these VOCs have attracted the attention of physicians, physiologist, and surgeons as potential aids to clinical diagnosis and therapeutic monitoring.[11] Recent studies have demonstrated that sniffer dogs can differentiate patients from control negative by sniffing their urine.[12-15] In particular with PCa, the sensitivities and specificities are both 91% or higher.[13,16,17] RCCs are epithelial tumors in contact with the urinary space[96], making this cancer well suited for a metabolomic approach through the VOCs analysis of urine. Additionally, VOCs can be readily detected by using analytic instruments, like gas chromatography-mass spectrometry (GC-MS), or further developed gas sensors.[18-21] All of those qualities, including non-invasiveness, non-injury, easy detection, high sensitivity and high specificity, make VOCs desirable disease markers. Certain embodiments are directed to or are related to the SBSE GC/MS Algorithmic Regression Technique to detect VOCs, aka SMART VOCs.

In one instance the inventors have detected VOCs in urine samples from 33 PCa patients and 41 controls. Logistic regression model was used to search the potential VOC markers for PCa specificity. And in depth literature study of some selected VOCs were investigated to better understand the metabolic significance of those VOCs.

In another instance the inventors have detected VOCs in urine samples from 108 men, 55 were diagnosed with PCa, while 53 were PCa negative controls. For the development of PCa risk model, an additional 34 PCa positive patients were included to attain 89 subjects in PCa risk assessment. Based on the Gleason score (GS) and PSA, these PCa patients were divided into two groups: low-risk group (GS=6, PSA<10) and high-risk group (GS=6 and PSA≥10, or GS>6 with any PSA values) as shown in Table 11. The high risk group was considered to be clinical significant and low risk group as indolent PCa. Logistic regression model was used to search the potential VOC markers for PCa. And in depth literature study of some selected VOCs were investigated to better understand the metabolic significance of those VOCs.

In another instance VOCs were detected in 111 urine samples from, (a) 77 patients preoperatively on the day of surgery who were undergoing partial or radical nephrectomy with a presumptive diagnosis of RCC based on a CT imaged renal mass and whose postoperative pathology diagnosis established clear cell, papillary or chromophobe RCC; (b) 24 patients were RCC negative based the imaged renal mass; and (c) 10-defined healthy controls. Logistic regression model was used to search the potential VOC markers for RCC. And in depth literature study of some selected VOCs were investigated to better understand the metabolic significance of those VOCs.

Certain embodiments are directed to methods of identifying a subject having prostate cancer, the method comprising the steps of: (a) obtaining a sample from the subject; (b) determining a level of at least one volatile organic compound associated with prostate cancer in the sample; and (c) comparing the level of the at least one volatile organic compound from the sample with the level of the at least one volatile organic compound in a negative control sample or to a reference value, wherein a significantly different level of the at least one volatile organic compound in the sample as compared to the level of the compound in the negative control sample or a reference value is indicative of the presence of prostate cancer in the subject. The sample can be a urine sample. In certain aspects the at least one volatile organic compound associated with prostate cancer is selected from 2-undecanone, N-(2-hydroxyethyl)-decanamide; 2-benzyl sulfonyl-benzimidazole, methyl 1-octadecenyl ether, bicyclo[4.2.0]octa-1,3,5-triene, 1-chloro-nonadecane, 3-methylene-4-phenyl-tricyclo[5.2.1.0(2,6)]decane, 1-decen-3-yne, 2-phenyl-2,2'-bi-1,3-dioxolane, 2-ethylacridine; N-[4-(trimethylsilyl)phenyl]-acetamide, 2-methoxy-2-methylbut-3-ene, N-methyltaurine; 1-bromo-tetracosane, methoxyacetic acid, and/or heptadecyl ester. In certain aspects the at least one volatile organic compound associated with prostate cancer is selected from 4-(3,4-dihydro-2, 2,4-trimethyl-2H-1-benzopyran-4-yl)-phenol, 1,1,3,3,5,5,7, 7,9,9-decamethyl-pentasiloxane, 1,1,1,5,5,5-hexamethyl-3, 3-bis[(trimethylsilyl)oxy], ethyl alpha-hydroxymyristate, 1-Propylpentachlorotriphosphazene, 4-Nitro-4'-chlorodiphenylsulfoxide, 1-(2,4-Dimethylphenyl)-3-(tetrahydrofuryl-2)propane, imidazole-5-carboxylic acid, 2-amino-; 2,6-di-t-butyl-4-hydroxymethylene-2,3,5,6-detetrahydrocyclohexanone, estradiol and/or phthalic acid bis(7-methyloctyl) ester. The level of at least one volatile organic compound in the sample can be determined by using of at least one technique selected from the group consisting of Gas-Chromatography (GC), GC-lined Mass-Spectrometry (GC-MS), Proton Transfer Reaction Mass-Spectrometry (PTR-MS), and Quartz Crystal Microbalance (QCM). In certain embodiments the subject is a male mammal. In particular aspects the subject is a human male. The term "significantly different" as used herein refers to a statistically significant quantitative difference between the levels. A statistically significant difference can be determined by any test known to the person skilled in the art. Common tests for statistical significance include, among others, t-test, ANOVA1 Kruskal-Wallis, Wilcoxon, Mann-Whitney, odds ratio, and regularized logistic regression. Individual samples (of unknown status) can be compared with data from the reference group (negative control), and/or compared with data obtained from a positive control group known to have prostate cancer. A set of control samples (positive and negative) or their digital equivalent can be stored as a reference collection for multiple analyses. An increase or decrease in the level as compared to a control or reference value or mean control level or reference value, or a change, difference or deviation from a control or reference value, can be considered to exist if the level differs from the control level or reference value, by about 5% or more, by about 10% or more, by about 20% or more, or by about 50% or more compared to the control level or reference value. The presence of a VOC marker which is absent in a control sample, is also contemplated as an increased level, deviation or change. The absence of a VOC marker which is present in a control, for example, is also contemplated as a decreased level, deviation or change.

Certain embodiments are directed to methods of prostate cancer risk assessment in a subject, the method comprising the steps of: (a) obtaining a sample from the subject; (b) determining a level of at least one volatile organic compound associated with prostate cancer risk assessment in the sample; and (c) comparing the level of the at least one volatile organic compound from the sample with the level of the at least one volatile organic compound in a control sample or to a reference value, wherein a significantly different level of the at least one volatile organic compound in the sample as compared to the level of the compound in the control sample or a reference value is indicative of the high risk or low risk of prostate cancer risk of the subject. The sample can be a urine sample. In certain aspects the at least one volatile organic compound associated with prostate cancer risk assessment is selected from tricyclo[4.3.1.1(3, 8)]undecane-3-carboxylic acid, methyl ester; 4-(1,1-dimethylethyl)-benzenepropanal; 5-octadecene, (E)-; acetaldehyde, butylhydrazone; 3,6-diamino-9-methylcarbazole; hexadecanoic acid, butyl ester; trans-3'-methyl-4-(methylthio)chalcone; 2-(1,1-dimethyl-2-propenyl)-3,6-dimethylphenol; 1-(2-butenyl)-2,3-dimethyl-benzene; (3alpha,5alpha)-androst-16-en-3-ol and/or metacetamol. The level of at least one volatile organic compound in the sample can be determined by using of at least one technique selected from the group consisting of Gas-Chromatography (GC), GC-lined Mass-Spectrometry (GC-MS), Proton Transfer Reaction Mass-Spectrometry (PTR-MS), and Quartz Crystal Microbalance (QCM). In certain embodiments the subject is a male mammal. In particular aspects the subject is a human male. The term "significantly different" as used herein refers to a statistically significant quantitative difference between the levels. A statistically significant difference can be determined by any test known to the person skilled in the art. Common tests for statistical significance include, among others, t-test, ANOVA1 Kruskal-Wallis, Wilcoxon, Mann-Whitney, odds ratio, and regularized logistic regression. Individual samples (of unknown status) can be compared with data from the reference group (negative control), and/or compared with data obtained from a positive control group known to have high risk or low risk prostate cancer. A set of control samples (high risk and low risk) or their digital equivalent can be stored as a reference collection for multiple analyses. An increase or decrease in the level as compared to a control or reference value or mean control level or reference value, or a change, difference or deviation from a control or reference value, can be considered to exist if the level differs from the control level or reference value, by about 5% or more, by about 10% or more, by about 20% or more, or by about 50% or more compared to the control level or reference value. The presence of a VOC marker which is absent in a control sample, is also contemplated as an increased level, deviation or change. The absence of a VOC marker which is present in a control, for example, is also contemplated as a decreased level, deviation or change.

Certain embodiments are directed to methods of identifying a subject having renal cell carcinoma, the method comprising the steps of: (a) obtaining a sample from the subject; (b) determining a level of at least one volatile organic compound associated with renal cell carcinoma in the sample; and (c) comparing the level of the at least one volatile organic compound from the sample with the level of the at least one volatile organic compound in a negative control sample or to a reference value, wherein a significantly different level of the at least one volatile organic compound in the sample as compared to the level of the compound in the negative control sample or a reference value is indicative of the presence of renal cell carcinoma in the subject. The sample can be a urine sample. In certain aspects the at least one volatile organic compound associated with prostate cancer is selected from cyclooctane; undecane; 1,2-benzenediol, 3,5-bis(1,1-dimethylethyl)-; 7H-bibenzo[β,γ]carbazole, 7-methyl-; imidazole-5-carboxylic acid, 2-amino-; acetamide, 2-(2,4-dimethoxybenzylidenehydrazino)-N-ethyl-2-oxo-; 4-Octynoic acid, 7-(t-butyldimethylsilyloxy)-, t-butyldimethylsilylester; 2-Cyclohexen-1-ol; Nonanal and/or 4-Nitro-4'-chlorodiphenylsulfoxide. The level of at least one volatile organic compound in the sample can be determined by using of at least one technique selected from the group consisting of Gas-Chromatography (GC), GC-lined Mass-Spectrometry (GC-MS), Proton Transfer Reaction Mass-Spectrometry (PTR-MS), and Quartz Crystal Microbalance (QCM). In particular aspects the subject is a human. The term "significantly different" as used herein refers to a statistically significant quantitative difference between the levels. A statistically significant difference can be determined by any test known to the person skilled in the art. Common tests for statistical significance include, among others, t-test, ANOVA1 Kruskal-Wallis, Wilcoxon, Mann-Whitney, odds ratio, and regularized logistic regression. Individual samples (of unknown status) can be compared with data from the reference group (negative control), and/or compared with data obtained from a positive control group known to have renal cell carcinoma. A set of control samples (positive and negative) or their digital equivalent can be stored as a reference collection for multiple analyses. An increase or decrease in the level as compared to a control or reference value or mean control level or reference value, or a change, difference or deviation from a control or reference value, can be considered to exist if the level differs from the control level or reference value, by about 5% or more, by about 10% or more, by about 20% or more, or by about 50% or more compared to the control level or reference value. The presence of a VOC marker which is absent in a control sample, is also contemplated as an increased level, deviation or change. The absence of a VOC marker which is present in a control, for example, is also contemplated as a decreased level, deviation or change.

Other embodiments include methods for treating prostate cancer, comprising: (i) determining that a patient has a prostate cancer according to methods of measuring or detecting the VOCs associated with prostate cancer as described herein; and (ii) administering a prostate cancer therapy to the patient determined to have prostate cancer.

Other embodiments include methods for treating prostate cancer, comprising: (i) determining that a patient has high risk of prostate cancer development according to methods of prostate cancer risk assessment in a subject or detecting the VOCs associated with prostate cancer risk assessment as described herein; and (ii) administering a prostate cancer therapy to the patient determined to have prostate cancer.

Other embodiments include methods for treating renal cell carcinoma, comprising: (i) determining that a patient has a renal cell carcinoma according to methods of measuring or detecting the VOCs associated with renal cell carcinoma as described herein; and (ii) administering a renal cell carcinoma therapy to the patient determined to have renal cell carcinoma.

The term "prostate cancer" refers to a neoplasm, e.g., malignant neoplasm, of the prostate within a given subject, wherein the neoplasm is of epithelial origin. The term "prostate cancer", when used without qualification, includes both localized and metastasized prostate cancer. The term "prostate cancer" can be qualified by the terms "localized" or "metastasized" to differentiate between different types of tumor as those words are defined herein.

The term "stage of prostate cancer" as used herein can be defined by one of a number of accepted systems for classifying the progression of prostate cancer. For example, the Jewett-Whitmore system classifies prostate cancer first as stage A, B, C, or D. Stages A and B cancers are considered curable. Stages C and D are treatable, but their prognoses are discouraging. A number is then assigned to describe specific conditions within each stage. For example, a tumor classified as stage B1 is a single cancerous nodule confined to one lobe of the prostate. More specifically, the stages are defined as follows: Stage A is very early and without symptoms; cancer cells confined to the prostate; Stage A1 is well differentiated and slightly abnormal cancer cells; stage A2 is moderately or poorly differentiated and abnormal cancer cells in several locations within the prostate; stage B is confined to the prostate, but palpable (detectable by digital rectal exam) and/or detectable by elevated PSA; stage B0 is confined to the prostate, nonpalpable; PSA elevated; stage B1 is a single cancerous nodule in one lobe of the prostate; stage B2 is extensive, involvement in one or both prostate lobes. Stage C is cancer cells found outside the prostate capsule (membrane covering the prostate); spread confined to surrounding tissues and/or seminal vesicles; stage C1 extends outside the prostate capsule; and stage C2 has bladder or urethral obstruction. Stage D has metastasis (spread) to regional lymph nodes, or to distant bones, organs (e.g., liver, lungs), and/or other tissues; stage D0 is metastatic, clinically localized, and showing elevated blood PAP levels; stage D1 has regional lymph nodes involved; stage D2 has distant lymph nodes, bones, or organs involve; and stage D3 has metastatic disease after treatment.

Alternatively, the TNM System may be used to stage prostate cancer. The TNM (tumor, node, metastases) system stages are similar to those of the Jewett-Whitmore system, but with more specific alphanumeric subcategories. Stages of prostate cancer according to the TNM system are Primary tumor (T), TX: tumor cannot be assessed; T0: no evidence of primary tumor; T1: clinically not palpable or visible by imaging; T1a: found incidental to other surgery; present in 5% or less of tissue; T1b: found incidental to other surgery; present in 5% or more of tissue; T1c: identified by needle biopsy; T2: tumor confined within prostate; T2a: involving half a lobe or less of prostate; T2b: involving half a lobe; T2c: involving both lobes; T3: tumor extends through prostate capsule; T3a: extends through one lobe; T3b: extends through both lobes; T3c extends into seminal vesicles; T4: involves structures other than seminal vesicles; T4a: invades bladder neck, external sphincter, or rectum; and T4b: invades muscles and/or pelvic wall. Regional Lymph Nodes (N); NX: Nodes cannot be assessed; N0: no regional node metastasis; N1: single node metastasis, 2 centimeters (cm) or less at largest point; N2: single node metastasis, 2 cm to 5 cm at largest point, or multiple nodes, no larger than 5 cm at largest point; N3: metastasis larger than 5 cm in any node; Distant Metastasis (M): MX: metastasis cannot be assessed; M0: no distant metastasis; M1: distant metastasis: M1a: distant lymph node(s) involved; M1b: bone(s) involved; M1c: other site(s) involved.

Prostate cancer is classified into different risk categories, including low-risk, and high-risk prostate cancer, which means that a patient has a low, and high-risk, respectively, of pathological and biochemical outcomes after radical prostatectomy; metastasis; prostate cancer-specific mortality; and all-cause mortality. One means of assessing the risk is using Gleason scoring and PSA: low-risk prostate cancer, Gleason score (GS)≤6 and PSA<10; high-risk prostate cancer, GS≤6 and PSA≥10, or GS>6 for all PSA level.

"Renal cell carcinoma" or "RCC" refers to human kidney cancer classified as being of at least one of the following histologies: clear cell RCC, papillary RCC (type 1 or type 2), chromophobe RCC, oncocytoma RCC. Typically, the RCC is at least a clear cell carcinoma but RCC patients collectively may exhibit 2, 3, or all 4 histologies. level.

Within the context of the invention, the term "true positives" refers to those subjects having a localized or a metastasized prostate cancer or RCC.

Within the context of the invention, the term "false negatives" refers to those subjects having either a localized or a metastasized prostate cancer or RCC and are not categorized as such by a diagnostic assay.

Within the context of the invention, the term "true negatives" refers to those subjects who do not have a localized or a metastasized prostate cancer or RCC and who are not categorized as such by a diagnostic assay.

Within the context of the invention, the term "false positives" refers to those subjects who do not have a localized or a metastasized prostate cancer or RCC but are categorized by a conventional diagnostic assay as having a localized or metastasized prostate cancer or RCC. Depending on context, the term "false positives" may also refer to those subjects who do not have prostate cancer or RCC but are categorized by a diagnostic assay as having prostate cancer or RCC or a non-malignant disease of the large intestine.

The term "sensitivity", as used herein in the context of its application to diagnostic assays, refers to the proportion of all subjects with localized or metastasized prostate cancer or RCC that are correctly identified as such (that is, the number of true positives divided by the sum of the number of true positives and false negatives).

The term "specificity" of a diagnostic assay, as used herein in the context of its application to diagnostic assays, refers to the proportion of all subjects with neither localized or metastasized prostate cancer or RCC that are correctly identified as such (that is, the number of true negatives divided by the sum of the number of true negatives and false positives).

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa.

The use of the word "a" or "an" when used in conjunction with the term "comprising" in the claims and/or the specification may mean "one," but it is also consistent with the meaning of "one or more," "at least one," and "one or more than one."

The term "about" or "approximately" are defined as being close to as understood by one of ordinary skill in the art. In one non-limiting embodiment the terms are defined to be within 10%, preferably within 5%, more preferably within 1%, and most preferably within 0.5%.

The term "substantially" and its variations are defined to include ranges within 10%, within 5%, within 1%, or within 0.5%.

The terms "inhibiting" or "reducing" or "preventing" or any variation of these terms includes any measurable decrease or complete inhibition to achieve a desired result.

The term "effective," as that term is used in the specification and/or claims, means adequate to accomplish a desired, expected, or intended result.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods of making and using the same of the present invention can "comprise," "consist essentially of," or "consist of" particular ingredients, components, blends, method steps, etc., disclosed throughout the specification.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DETAILED DESCRIPTION OF THE INVENTION

Prostate cancer (PCa) is the second most common cause of male cancer specific mortality in the United States. Though early detection of PCa is critical to treating the disease, the lack of sensitivity and selectivity of prostate specific antigen (PSA) in PCa screening has stimulated an intense search for more reliable VOCs of the disease. Recent studies have demonstrated that dogs can differentiate PCa patients from control negative by sniffing their urine. As the odor profiles are constituted by volatile organic compounds (VOCs), the inventors sought to identify PCa-specific VOCs in urine for PCa diagnosis and prognosis.

In one instance the inventors conducted a study that included 74 men (aged from 40 to 84) who presented for trans-rectal ultrasound guided prostate biopsy for an elevated serum PSA (>2.5 ng/mL) or abnormal digital rectal exam. Of the 74 men, 33 were diagnosed with PCa. PSA levels ranged from 2.66 to 1987 in men with PCa vs 0.45 to 11.42 in men without PCa. All VOCs were identified based on their occurrence and relative quantity in the urine. Potential PCa-specific VOCs were screened by Wilcoxon rank-sum tests. Logistic regression was applied to develop models for using VOC markers in PCa diagnosis. In terms of the bivariate association with PCa prevalence, 37 VOCs were found to be related to PCa positive urine samples while 45 VOCs corresponding to PCa negative ones $1_1$ with statistical significance at $\alpha=0.05$. Applying a liberal cutoff of 0.20 on the p-values, 258 potential VOCs were identified and used for further model development. After further selection with $1_1$ regularization, the final logistic model involves 15 VOCs only. On the basis of predicted probabilities from the final model via cross-validation, the area under the receiver operating characteristic curve is 0.943, which indicates a highly promising discrimination power of urinary VOCs in PCa positive and negative patients.

Figure 6:
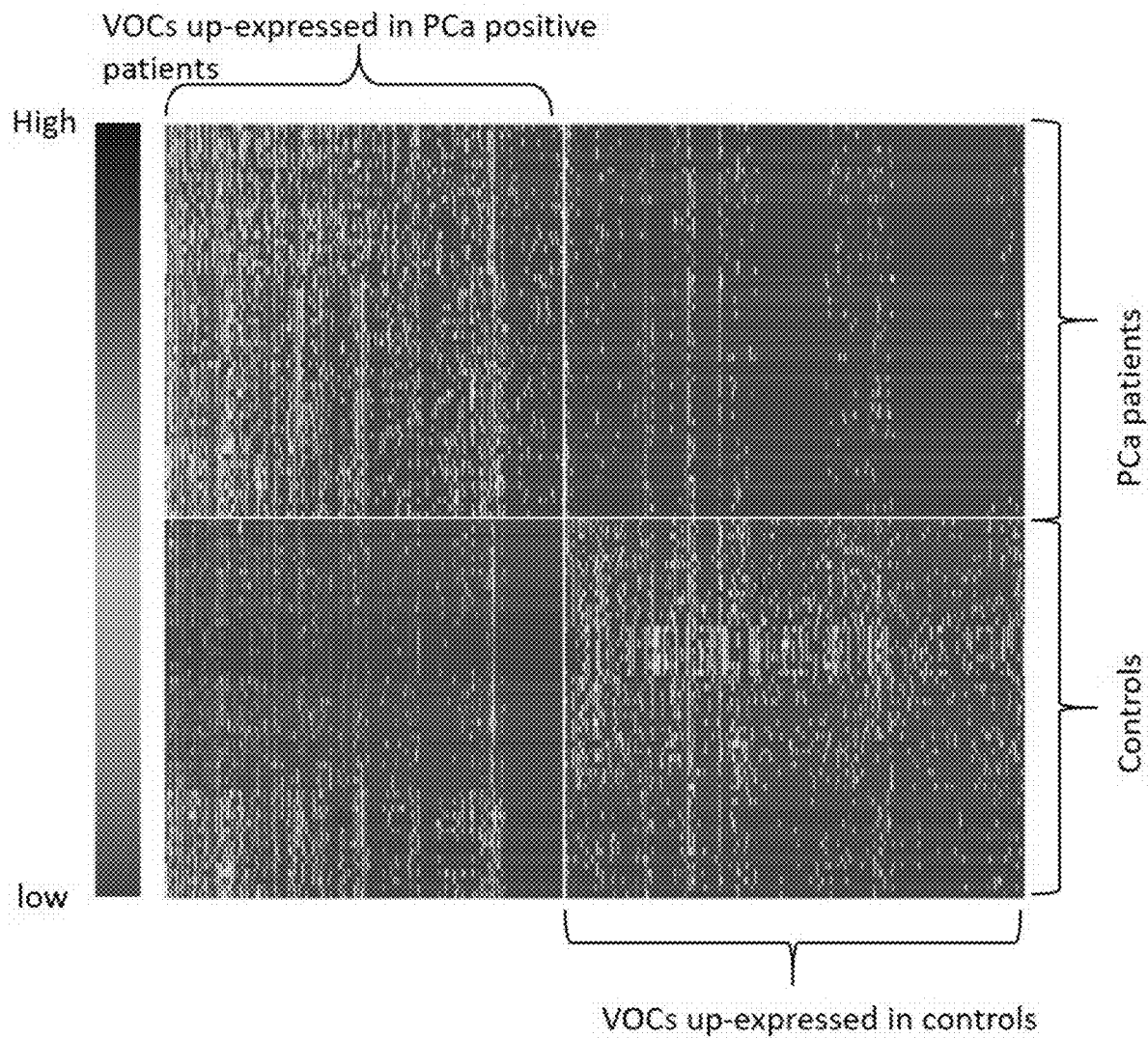
FIG. 6. Illustrates a heat map of selected VOCs (p<0.05) in Wilcoxon test of prostate cancer samples vs controls of example 3. The correlation between VOCs and patients ranges from low (red) to high (blue).
Figure 7A:
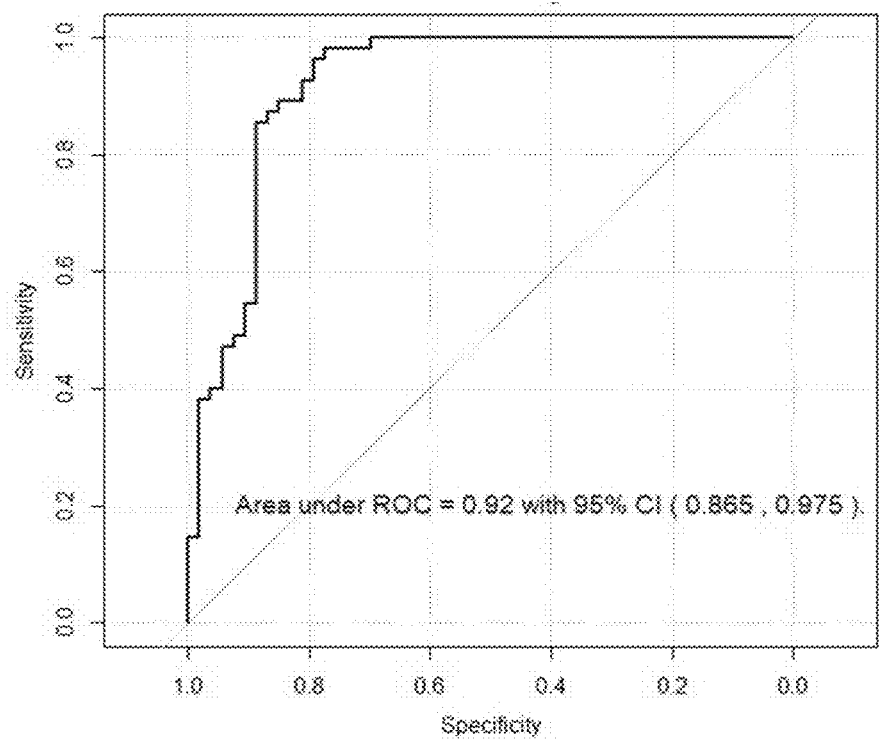
FIGS. 7A-B. Illustrates (A) ROC curve for prostate cancer diagnosis logistic regression model (Jackknife analysis) with 11 selected VOCs; (B) ROC curve for prostate cancer diagnosis logistic regression model with PSA only; Both models were evaluated in the same 108 patients of example 3.
Figure 7B:
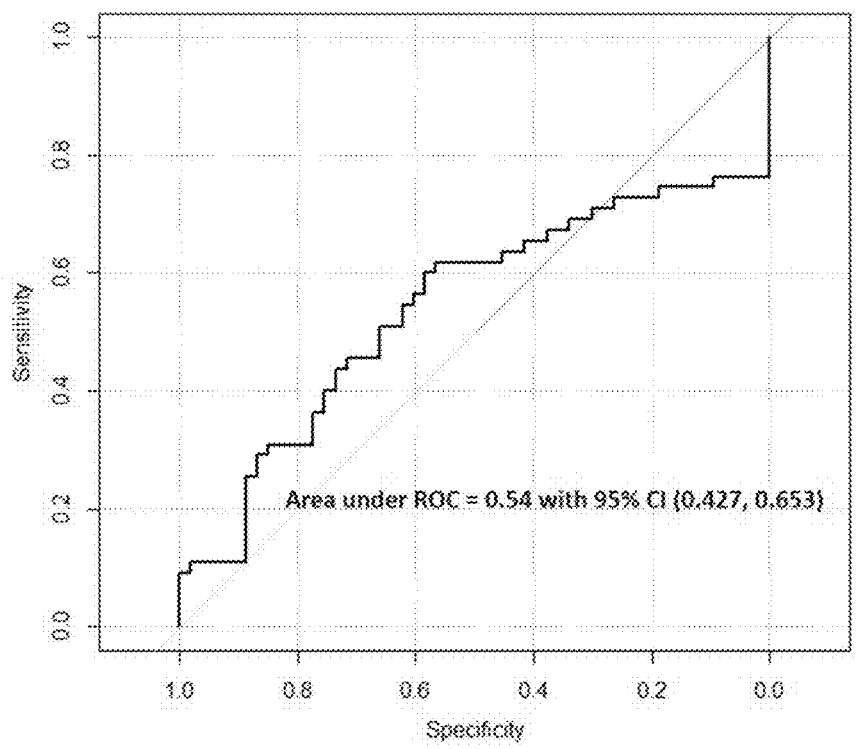

In one instance a total of 9,144 potential VOCs were detected in urine collected from 108 patients (aged from 40 to 80). Of the 108 men, 55 were diagnosed with PCa, while 53 were PCa negative controls. For the development of PCa risk model, additional 34 PCa positive patients were included to attain 89 subjects in PCa risk assessment. Based on the Gleason score (GS) and PSA, these prostate cancer patients were divided into two groups: low-risk group (GS=6, PSA<10) and high-risk group (GS=6 and PSA≥10, or GS>6 with any PSA values) as shown in Table 11. The high risk group was considered to be clinical significant and low risk group reflected indolent PCa. Using the Wilcoxon test at statistical significance p<0.05, 254 VOCs were found to be related to prostate cancer positive urine samples and 282 VOCs corresponding to prostate cancer negative ones. The distribution of those selected VOCs in patients was shown in FIG. 6. A broader range of VOCs were selected into the regression model (cutoff at p=0.20), and 850 potential VOCs were identified. After further selection with $1_1$ regularization, 11 VOCs were selected for the final logistic model (listed in the Table 12). On the basis of predicted probabilities from the final model via jackknife cross-validation, the area under the receiver operating characteristic (ROC) curve (AUC) was 0.92 as shown in FIG. 7A, which indicated a highly promising discrimination power between VOCs in urine of PCa positive and controls. As a comparison, the diagnostic performance of PSA were also tested. The prediction model rendered an AUC of 0.54 and the sensitivity and specificity were 0.44 and 0.74 respectively, indicating a poor discriminating ability of PSA in PCa diagnosis (FIG. 7B). Using Wilcoxon rank sum test, 23 VOCs were found to be highly related to high-risk PCa and 44 VOCs corresponding to the low risk PCa shown in FIG. 8. After variable screening with a more liberal cutoff at p=0.20, 289 potential VOCs were selected for model development. Using $1_1$ regularization, the final logistic model selected 11 VOCs (listed in the Table 12). On the basis of predicted probabilities from the final model via Jackknife cross-validation, the area under the receiver operating characteristic (ROC) curve is 0.86 as shown FIG. 9, which indicates a highly promising discrimination power of urinary VOCs in PCa high risk assessment.

A. Diagnostic Methods

The present invention relates to methods for differential diagnosis of prostate cancer by detecting one or more differentially produced VOCs in a biological sample of a given subject, wherein the presence or absence of the VOCs allows for the differential diagnosis of a subject as healthy or having prostate cancer. In one embodiment, the methods detect the presence of a VOC in a sample wherein the VOC is not produced or present in healthy, disease-free individuals. In related embodiments, the methods of the invention detect elevated levels of VOCs that are present at higher levels in samples from individuals that have cancer, e.g., prostate cancer, as compared to normal, healthy individuals.

In one embodiment, the diagnostic methods of the invention are particularly useful in subjects that have PSA levels of less than 10. Accordingly, the instant invention provides methods for the early detection of prostate cancer in subjects who, using currently available methods, would not be diagnosed with prostate cancer until the disease progresses, i.e., until the PSA levels or other symptoms or diagnostic markers in these subjects reached a higher level.

In one aspect of the invention, a method for the differential diagnosis of prostate cancer comprises: obtaining a biological sample from a given subject, detecting one or more VOC using a detection method, wherein the detection method generates a profile of one or more VOC in the sample, and comparing or assessing the VOC profile of the sample with a control or a database containing profiles from comparable samples or reference levels for healthy subjects, subjects having prostate cancer, and/or subjects having a related non-malignant disease of the prostate. The outcome of said comparison will allow for the determination of whether the subject from which the biological sample was obtained, is healthy, has a non-malignant disease of the prostate, or prostate cancer based on the presence, absence or comparative quantity of specific VOCs.

In more than one embodiment, a single VOC or a combination of more than one VOC selected may be detected within a given biological sample.

In yet another aspect of the invention, a VOC may be used in combination with another diagnostic tool to diagnose a subject as being healthy or having prostate cancer. For example, levels of a VOC may be used in combination with other diagnostic tools specific for prostate cancer detection such as, but not limited to, rectal palpitation, biopsy evaluation using Gleason scoring, radiography and symptomological evaluation by a qualified clinician or determination of PSA levels. In addition, methods of the invention for the differential diagnosis of healthy subjects or subjects having a prostate cancer may be combined with other diagnostic methods to improve the outcome of the differential diagnosis. Other diagnostic methods such as PSA screening are well known.

B. Biological Samples of the Invention

Although VOCs were first identified in urine samples, their detection is not limited to this sample type. In more than one embodiment of the invention, VOCs can be detected and/or measured in blood, plasma, urine, semen, seminal fluid, seminal plasma, pre-ejaculatory fluid (Cowper's fluid), excreta, tears, saliva, sweat, biopsy, ascites, cerebrospinal fluid, lymph, or tissue extract (biopsy) samples. Preferably, biological samples used to detect VOCs of the invention are of urine, blood, serum, plasma and excreta, particularly urine.

Furthermore, biological samples used for methods of the invention are isolated from subjects of mammalian origin, preferably of primate origin. Even more preferred are male subjects of human origin.

A subject that is said to have prostate cancer possesses morphological, biochemical, and functional alterations of their prostate tissue such that the tissue can be characterized as a malignant neoplasm. The stage to which a prostate cancer has progressed can be determined using known methods currently available and presented herein. Currently, the most widely used method for determining the extent of malignancy of a prostate neoplasm is the Gleason Grading system. Gleason grading is based exclusively on the architectural pattern of the glands of a prostate neoplasm, wherein the ability of neoplastic cells to structure themselves into glands resembling those of the normal large intestine is evaluated using a scale of 1 to 5. For example, neoplastic cells that are able to architecturally structure themselves such that they resemble normal gland structure are graded 1-2, whereas neoplastic cells that are unable to do so are graded 4-5. A prostate neoplasm has tumor structure that is nearly normal will tend to behave, biologically, as normal tissue and therefore it is unlikely that it will be aggressively malignant.

A subject that is said to have non-malignant disease possesses morphological and/or biochemical alterations of their prostate tissue but does not exhibit malignant neoplastic properties. Such diseases include, but are not limited to, inflammatory and proliferative lesions, as well as benign disorders.

C. Detection of VOC of the Invention

The one or more VOCs may be detected using various technologies including, but not limited to: gas chromatography (GC); liquid chromatography (LC); spectrometry, for example mass spectrometry (including quadrupole, time of flight, tandem mass spectrometry, ion cyclotron resonance, and/or sector (magnetic and/or electrostatic)), ion mobility spectrometry, field asymmetric ion mobility spectrometry, and/or DMS; fuel cell electrodes; light absorption spectroscopy; nanoparticle technology; flexural plate wave (FPW) sensors; biosensors that mimic naturally occurring cellular mechanisms; electrochemical sensors; photoacoustic equipment; laser-based equipment; electronic noses (bio-derived, surface coated); various ionization techniques; and/or trained animal detection.

In certain embodiments, the diagnostic device can include electronics capable of storing a library of information about VOCs that are indicative of various conditions. Alternatively, the electronics can allow for connectivity to one or more remote databases. In the library or databases, previously collected and/or known VOC data may be associated with certain conditions and/or include associations with other relevant information.

D. Treatment of Prostate Cancer

Differential production or presence of VOCs in samples from healthy subjects and subjects having prostate cancer allows for a differential diagnosis of prostate cancer in a given subject. In certain embodiments, the methods further comprise managing subject treatment based on the status determined by the methods described herein. In certain embodiments the methods can qualifying prostate cancer status, the methods further comprise managing subject treatment based on the status or determination of the methods described herein. Such management includes the actions of the physician or clinician subsequent to determining prostate cancer status. For example, if a physician makes a diagnosis of prostate cancer, then a certain regime of treatment, such as prescription or administration of therapeutic agent might follow. Alternatively, a diagnosis of non-prostate cancer or other prostate condition might be followed with further testing to determine a specific disease that might the patient might be suffering from. Also, if the diagnostic test gives an inconclusive result on prostate cancer status, further tests may be called for.

E. Treatment of Renal Cell Carcinoma

Differential production or presence of VOCs in samples from healthy subjects and subjects having renal cell carcinoma allows for a differential diagnosis of renal cell carcinoma in a given subject. In certain embodiments, the methods further comprise managing subject treatment based on the status determined by the methods described herein. In certain embodiments the methods can qualifying renal cell carcinoma status, the methods further comprise managing subject treatment based on the status or determination of the methods described herein. Such management includes the actions of the physician or clinician subsequent to determining renal cell carcinoma status. For example, if a physician makes a diagnosis of renal cell carcinoma, then a certain regime of treatment, such as prescription or administration of therapeutic agent might follow. Alternatively, a diagnosis of non-renal cell carcinoma might be followed with further testing to determine a specific disease that might the patient might be suffering from. Also, if the diagnostic test gives an inconclusive result on renal cell carcinoma status, further tests may be called for.

EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Volatile Organic Compounds in Urine of Prostate Cancer Patients

A. Results

The 33 PCa samples were compared with the 41 PCa negative control samples to look for the symbolic VOCs for PCa diagnosis. All of VOCs from urine samples were analyzed by GC-MS and identified with NIST (National Institute of Standards and Technology) compound library. Those VOCs were then subjected to statistical analysis, for their significance in PCa diagnosis.

VOCs identified by using TD-GC/MS and NIST. The identification of VOCs profile in urine samples was based on the Chemstation (Agilent) NIST Library Search Report. The relative intensity of each peak was normalized against that of the internal standard, Mirex, in chromatogram analysis. The internal standard was chosen because of its non-existence in urine samples. The relative peak area ratio of specific VOC and mirex was used to do semi-quantitative analysis of each VOC in urines. In each urine sample, the number of VOCs detected by GC/MS was varied from 172 to 225. A total of about 6,000 VOCs were identified in 77 urine samples.

Figure 1:
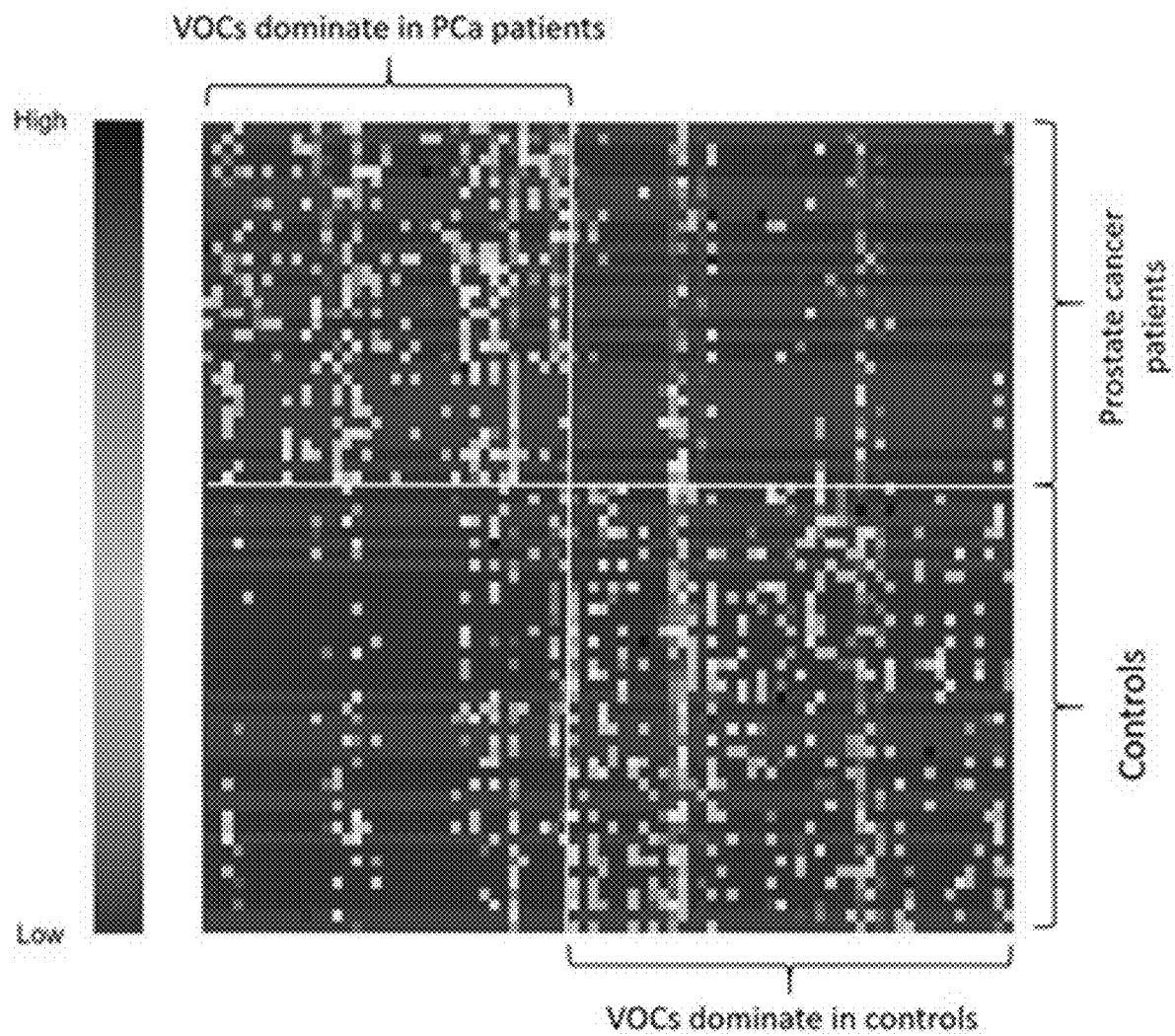
FIG. 1. Illustrates a heat map of selected VOCs (p<0.05) in Wilcoxon test of prostate cancer samples vs controls of example 1. The correlation between VOCs and patients ranges from low to high.

Prostate cancer samples vs. controls. Using the Wilcoxon test at statistical significance $\alpha=0.05$, 37 VOCs were extracted for exploratory purposes to be related to PCa positive urine samples and 45 VOCs corresponding to PCa negative ones. The distribution of those selected VOCs in patients is shown in FIG. 1.

Figure 2:
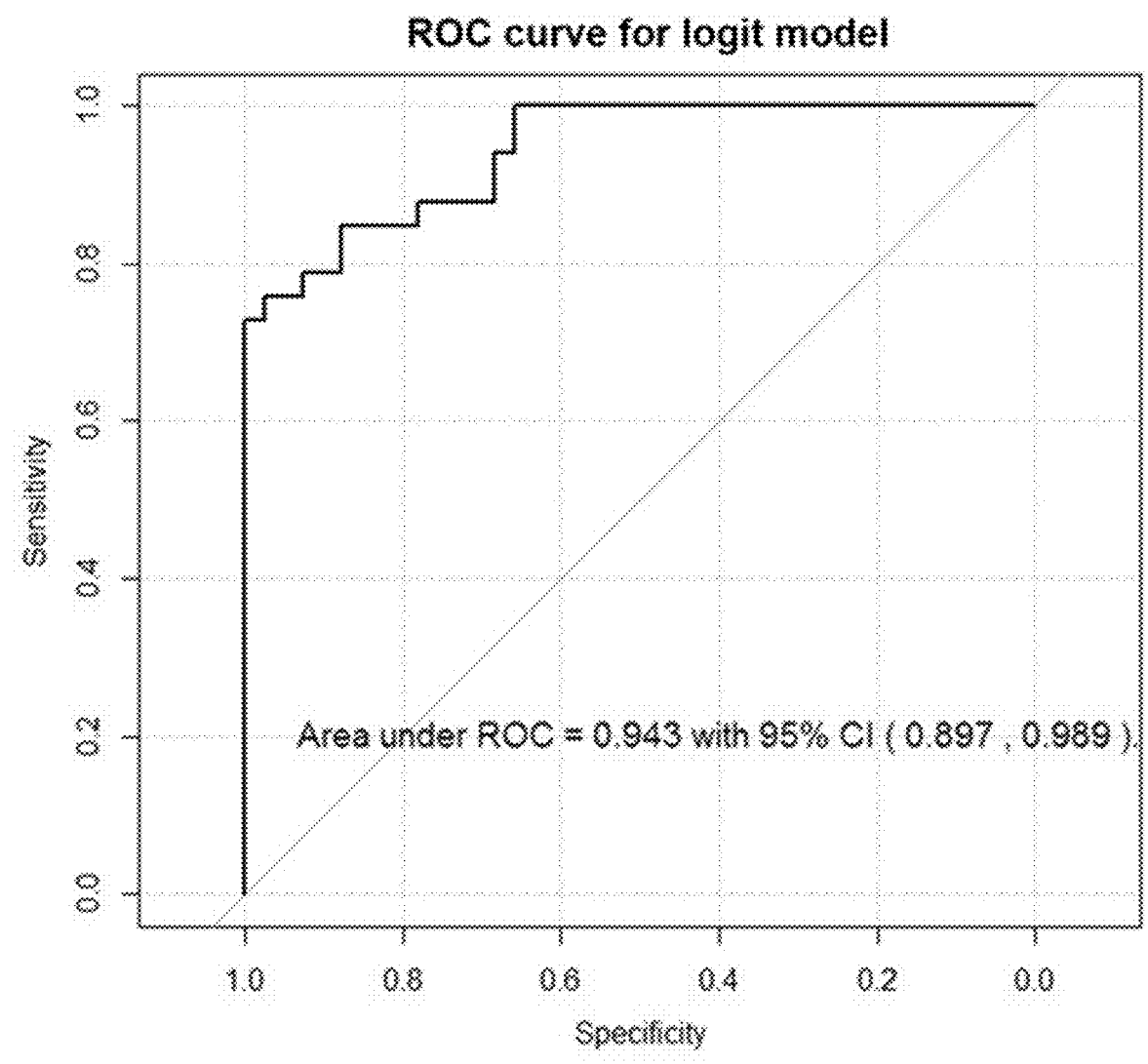
FIG. 2. Is an example of a Receiver Operating Characteristic (ROC) curve for prostate cancer diagnosis logistic model with 15 selected VOCs verified in 75 patients, of example 1.

After variable screening with a more liberal cutoff of $\alpha=0.20$, 258 potential VOCs were identified. After further selection with regularization, the final logistic model selected 15 VOCs, including 2-undecanone, N-(2-hydroxyethyl)-decanamide; 2-benzyl sulfonyl-benzimidazole, methyl 1-octadecenyl ether, bicyclo[4.2.0]octa-1,3,5-triene, 1-chloro-nonadecane, 3-methylene-4-phenyl-tricyclo [5.2.1.0(2,6)]decane, 1-decen-3-yne, 2-phenyl-2,2'-bi-1,3-dioxolane, 2-ethylacridine; N-[4-(trimethylsilyl)phenyl]-acetamide, 2-methoxy-2-methylbut-3-ene, N-methyltaurine; 1-bromo-tetracosane, methoxyacetic acid, and heptadecyl ester. On the basis of predicted probabilities from the final model via jackknife cross-validation, the area under the receiver operating characteristic (ROC) curve is as high as 0.943 as shown in FIG. 2, which indicates a highly promising discrimination power between VOCs in urine of PCa positive and controls.

Figure 3A:
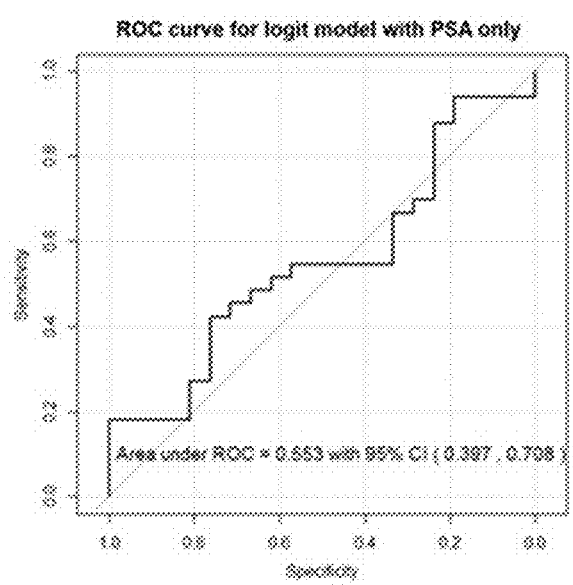
FIGS. 3A-B. Illustrates (A) The ROC curve for prostate cancer diagnosis logistic regression model (Jackknife analysis) with PSA; (B) The ROC curve for prostate cancer diagnosis logistic regression model with 15 selected VOCs. Both models were evaluated in the same 54 patients of example 1.
Figure 3B:
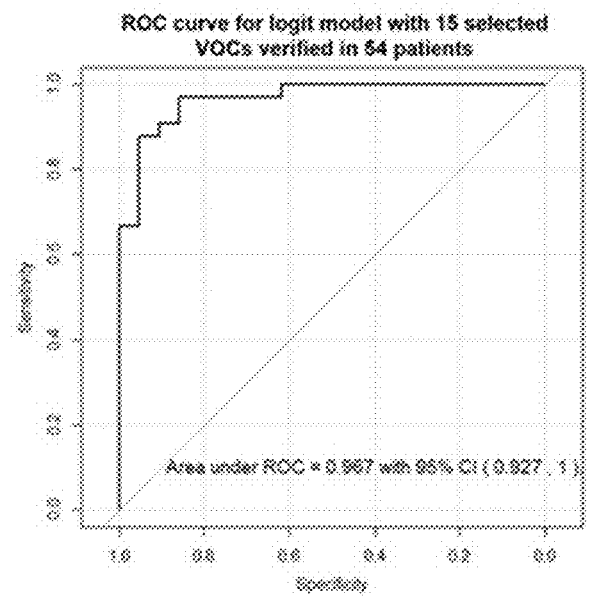
Figure 4A:
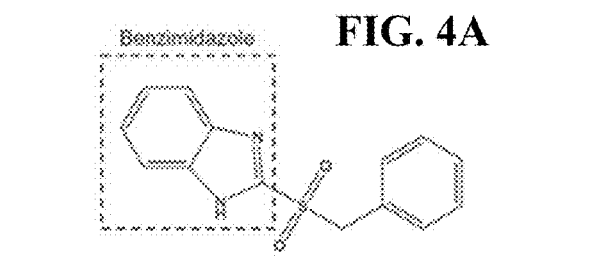
FIGS. 4A-D. Illustrates the chemical structure of (A) benzimidazole, 2-benzylsulfonyl-; (B) Bicyclo[4.2.0]octa-1, 3,5-triene; (C) Decanamide, N-(2-hydroxyethyl)-; and (D) N-Methyltaurine.
Figure 4B:
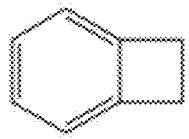
Figure 4C:
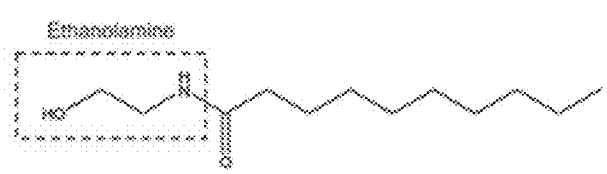
Figure 4D:
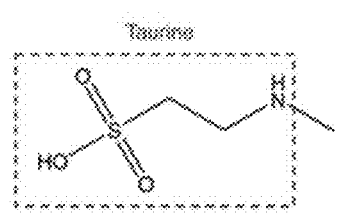

PSA vs VOCs selected in logistic regression model. As mentioned above, the selected VOCs pattern has exhibited outstanding discrimination power in PCa diagnosis. As a comparison, the diagnostic performance of PSA in differentiating PCa samples from controls were also tested. PSA values for 54 patients out of 74 are available and were used in this study. Among those samples, 33 urine samples were from PCa subjects while 21 were of PCa negative controls. PSA in PCa prediction was assessed in those patients through Jackknife analysis. The area under ROC curve is only 0.553, which shows a poor discriminated performance in FIG. 3A. The sensitivity and the specificity were found to be 0.47 and 0.71 respectively. In comparison, the inventors used the same sample pool to validate the VOC logistic model as aforementioned using 15 VOCs. The area under ROC curve of those selected VOCs is 0.967 as shown in FIG. 3B. The sensitivity of those selected VOCs performance was 0.85 and specificity was 0.86. All those results indicate that the selected VOCs show higher discrimination power in PCa diagnosis than PSA could accomplish.

Many on-going efforts are focused on improving PSA testing. The structure-based Iso-PSA has been reported to have better diagnostic accuracy for detecting PCa in a cohort of men undergoing biopsy for standard clinical indications than a standard concentration-based PSA assay. The area under ROC curve is around 0.80, but the specificity of IsoPSA is around 45%, which could lead to over-diagnosis in PCa-negative patients.[22]

In contrast, urinary VOCs based logistic regression model in this study showed much better diagnostic performance than PSA and iso-PSA. The sample preparation process is simple and easy, which provides the benefit of low operating cost and minimal technical training of personnel. Using the solventless sample preparation technique, named Stir Bar Sorptive Extraction, can preserve the sample integrity and allows effective analysis for processing large sample size. Unlike GC-sensor (such as E-nose),[23] the GC/MS coupled with NIST library used in this study provided much detailed information for future physiological studies. Through the application of a variety of advanced statistical analysis tools (Wilcoxon rank-sum test, logistic regression model, cross validation), urinary VOCs performed excellent discrimination power in PCa diagnosis. The Wilcoxon rank-sum test is a nonparametric alternative to the two sample t-test which is based solely on the order in which the observations from the two samples fall.[24] Since it makes no assumptions on the distribution of the explanatory data, logistic regression is widely used flexible and robust multivariate statistical methods for data analysis.[25] Cross validation has been proved to be better accuracy estimation methods than others, like holdout and bootstrap.[26] All those less-conditional statistical methods make the data analysis of urinary VOCs much easier to be processed.

After the cross-validation of selected VOCs from logistic regression models of PCa positive samples vs PCa negative samples, the area under ROC curve was 0.94 (FIG. 2), which indicate the highly promising discrimination power between VOCs in urine of PCa diagnosis. The area under ROC curve, 0.943, is also higher than the value recently reported by Khalid T, et al in 2015.[20] It may owe to the simple sample preparation and stir bar sorptive extraction, which help to extract most VOCs in urine samples.

The results show that VOCs has better performance in differentiating PCa samples from controls than PSA. A total of 15 VOCs were selected by the logistic model used in the described study. Among them, 10 VOCs were up-regulated, i.e., dominated in PCa positive patients (risk group), while the remaining 5 VOCs were dominated in PCa negative patients (curing group). The compounds and their belonging groups are listed in Table 1. Several of them have presented physiological significance (FIG. 4). For instance, bicyclo [4.2.0]octa-1,3,5-triene, a VOC in the risk group, was also found by Hossam Haick and his co-workers in exhaled breath of lung cancer patients.[18] In this paper, bicyclo[4.2.0] octa-1,3,5-triene existed in much higher abundance in lung cancer patients than in healthy controls.[18] Then, bicyclo [4.2.0]octa-1,3,5-triene may also be involved in PCa progression.

TABLE 1

Fifteen Selected VOCS From Logistic Regression Model.

| Chemical Name | CAS Number | Cancer Positive/ Cancer Negative Group |
|---|---|---|
| 2-Undecanone | 000112-12-9 | Cancer Negative |
| Decanamide, N-(2-hydroxyethyl)- | 007726-08-1 | Cancer Negative |
| Benzimidazole, 2-benzylsulfonyl- | 100872-42-2 | Positive |
| Ether, methyl 1-octadecenyl | 026537-06-4 | Positive |
| Bicyclo[4.2.0]octa-1,3,5-triene | 000694-87-1 | Positive |
| Nonadecane, 1-chloro- | 062016-76-6 | Cancer Negative |
| Tricyclo[5.2.1.0(2,6)]decane, 3-methylene-4-phenyl- | 1000150-37-1 | Positive |
| 1-Decen-3-yne | 033622-26-3 | Positive |
| 2,2'-Bi-1,3-dioxolane, 2-phenyl- | 021504-04-1 | Positive |
| 2-Ethylacridine | 055751-83-2 | Cancer Negative |
| Acetamide, N-[4-(trimethylsilyl)phenyl]- | 017983-71-0 | Positive |
| 2-Methoxy-2-methylbut-3-ene | 040426-44-6 | Positive |
| N-Methyltaurine | 000107-68-6 | Positive |
| Tetracosane, 1-bromo- | 006946-24-3 | Positive |
| Methoxyacetic acid, heptadecyl ester | 1000282-99-1 | Cancer Negative |

Another interesting compound in the risk group is 2-benzylsulfonyl-benzimidazole. The "benzimidazole" moiety is one of the so called "privileged substructures" which means it has diverse portfolio of biological activities. The stimulus for preparing Galeterone, (TOK-001 or VN/124-1), a C-17-heteroaryl steroidal CYP17 inhibitor and anti-androgen, was based on the desire to incorporate the benzimidazole moiety in the structure.[27-30] Galeterone is a first-in-class, multi-target, and oral small molecule in the development for the PCa treatment.[30] Galeterone binds with the nitrogen of the C17 benzimidazole forming a coordinate covalent with heme iron in the structure of CYP17A1.[31] In addition, one novel 2-aryl benzimidazole derivative was reported to exhibit antitumor activity, which blocked EGFR and HER2 activity and upregulates DR5 in breast cancer cells.[32] EGFR and HER2 are cell surface receptor tyrosine kinases and also reported to be involved in PCa metastasis to the bone.[33] Since all the urine samples collected in this study is prior to all of the treatments, the benizimidazole derivatives found in patients' urine may indicate some unknown biological functions highly related with PCa.

N-Methyltaurine is also one of compounds identified in the risk group. The moiety of "taurine" is a phylogenetically ancient compound with a disjunct distribution in the biosphere.[34] According to the study of metabolic characteristics of normal and malignant prostate, tumors have long been known to exhibit altered metabolic profiles and bioenergetics requirements.[35] Metabolite level of taurine in body fluids, such as urine and serum, as well as in tissue biopsies has been correlated with PCa progression; and the change of taurine level, when analyzed globally, could be a potential strategy for distinguishing indolent from aggressive disease.[36] Increasing levels of taurine in plasma samples of patients with bone metastases were observed, compared to those without.[37,38] The metabolic abundance profiles in localized and metastatic PCa, obtained in the study of Sreekumar et al[39], suggested that methyl transferase activity is a hallmark of PCa progression. Interestingly, N-Methyltaurine found in the urine samples in the inventors' study is verifies a methylation product of taurine.

Figure 5:
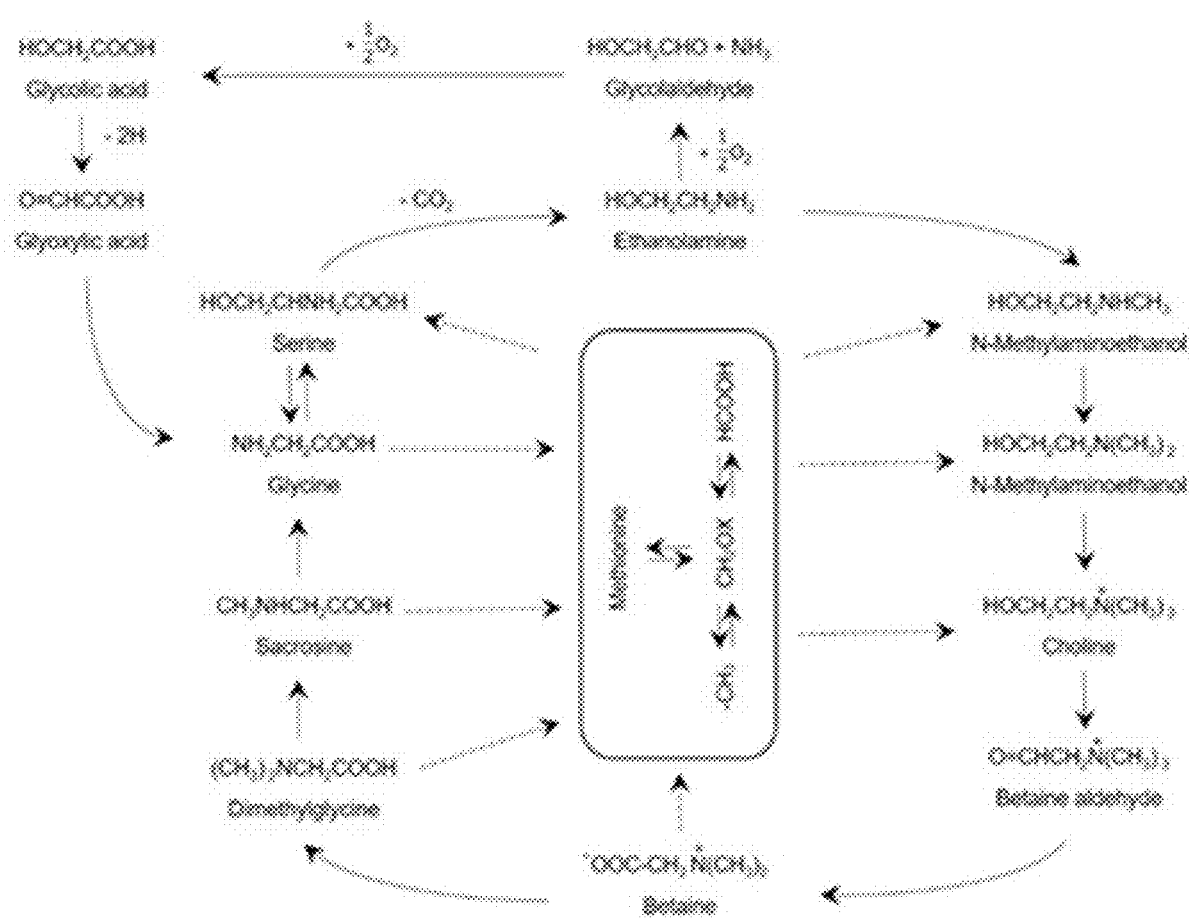
FIG. 5. Illustrates a hypothetical cycle of metabolism involving glycine, serine, ethanolamine, choline, and betaine. (Greenberg, D. M. Chemical pathways of metabolism. (Academic Press, 2014))

In the structure of N-(2-hydroxyethyl)-decanamide, a compound in curing group, the moiety of ethanolamine can be formed through the decarboxylation of serine or the reduction of glycine in vivo.[40-42] Ethanolamine, serine, glycine and sarcosine are closely interrelated in the body and, in fact, appear to form part of a metabolic cycle which may be represented as shown in FIG. 5.[42] One-carbon metabolism in vivo integrates cellular nutrient status by cycling carbon units from amino acid inputs to generate diverse outputs, including redox maintenance and cellular biosynthesis. Genetic and functional evidence also suggests that hyper activation of this pathway is a driver of oncogenesis and establishes a link to cellular epigenetic status.[43] Sarcosine was identified as a candidate VOC for metastatic PCa.[39] A metabolomics study of urine from patients with benign prostatic disease, localized PCa, and metastatic PCa revealed that glycine metabolism is a predictor of metastatic cancer.[39] Ethanolamine, as an intermediate in metabolic cycle of all those amino acids, could be found in metabolites of the human body when in a healthy state, which could explain the higher abundance of N-(2-hydroxyethyl)-decanamide found in urine samples of this study. In contrary, ethanolamine may be all converted to serine, glycine or Sarcosine in cancer development resulting in a low level in PCa patient urine samples.[43,44]

In the curing group, some compounds, such as 2-undecanone, 1-chloro-nonadecane, methoxyacetic acid, heptadecyl ester; and 1-bromo-tetracosane may be involved in fatty acid metabolism.[45] The biological function of those compounds are still unknown.

VOCs in urine is a noninvasive and promising diagnostic method for PCa. The biological and chemical significance of those selected VOCs in this study could link specific VOCs to the PCa progression and could be further used in identified different level of PCa. Further metabolomic study could be carried out to understand the biological and chemical significance of significant VOCs in human body and PCa progression. Though the sample size in the study described herein is small, the model validation showed very high correlation between VOCs and PCa.

B. Methods

The inventors start with exploratory data analysis (EDA), which involves various numerical and graphical statistical methods to summarize and describe each variable and their bivariate associations depending on the type of variables.

The VOC-based diagnostic tool can be developed via predictive modeling. The collected data present an ultra-high dimensional (p>>n) modeling problem, which, especially the relatively small sample size, renders many predictive tools neither inappropriate nor inapplicable. Logistic regression for modeling PCa occurrence is used as the main approach and the inventors follow Fan and Lv (2010) in principle. First, the inventors remove VOC variables with unitary or almost (≤3 observations having values different from others) unitary values. Then the inventors perform variable screening of VOCs based on the nonparametric Wilcoxon rank-sum test owing to zero inflation among many VOCs. A liberal cutoff threshold of $\alpha=0.20$ for significance level is applied to screen VOCs in this step. Next, regularized logistic regression with either LASSO (Tibashiarni, 1996) or SCAD (Fan and Li, 2001) penalty is fit to the data, which provides further variable selection. Either 10-fold cross-validation or the generalized cross-validation (GCV) criterion is used to select the optimal tuning parameter, which leads to a final logistic model in these approaches. Finally, the final logistic model is evaluated via the Receiver Operating Characteristic (ROC) curve and its associated performance measures on the basis of its jackknife prediction (see, e.g., Kleinbaum and Klein, 2010). The jackknife cross-validation technique helps avoid over-optimism induced by variable selection. Furthermore, to deal with the (almost) complete separation in the data, Firth's (1993) approach is taken to fit the final logistic model.

To further demonstrate the usefulness and efficiency of the VOC-based diagnostic tool, an additional logistic model for PCa incidence is developed with PSA being the only predictor and compared with the VOC-based logistic model in terms of area under the ROC curve (AUC). All the analyses are performed using the open-source statistical computing package R (R Core Team, 2017).

Chemicals and Materials. The internal standard, Mirex (99.0%, Dr. Ehrenstorfer GmbH, Germany), was purchased from the National Institute of Standards and Technology (NIST). Methanol used in this study was used to prepare the 100 ppm Mirex solution and was purchased from Burdick & Jackson (Muskegon, Mich., USA). Hydrochloric acid (HCl, 37%) was purchased from Sigma-Aldrich (St. Louis, Mo., USA). All chemicals used were of analytical grade. Ultra-pure deionized water from Milli-Q system (Millipore, Bedford, Mass., USA) was used in the preparation of 2 M solutions of HCl and dilution urine samples.

Patient recruitment and sample collection. The study included 74 men (aged from 40 to 84) who presented for trans-rectal ultrasound guided prostate biopsy for an elevated serum PSA (>2.5 ng/mL) or abnormal digital rectal exam (Table 2); 33 of them were diagnosed with PCa while 41 were PCa negative controls. Urine samples from all those patients were collected before all the medical treatments. No particular restriction of water and food were applied to the patients. Upon collection, approximately 20 mL of urine samples were collected and stored in −80° C. freezer until chemical analysis.

TABLE 2

Demographic information of prostate cancer patients, cancer-negative controls and other cancers.

| | Prostate cancer patients | | | Controls | | |
|---|---|---|---|---|---|---|
| | Low grade (<7) | High grade (≥7) | p value[a] | PSA (available) | PSA (unavailable) | p value[b] |
| N | 10 | 23 | 0.34 | 21 | 20 | 0.26 |
| PSA | 7.99 (2.46-1987) 8.98 (2.46-78.09) | 7.53 (3.63-1987) | | 4.43 (0.45-11.42) N/A | N/A N/A | |
| Gleason score | 3-9 | | | N/A | N/A | |

Extraction of VOCs from urine samples. Urine samples were thawed in ice. In a 20 mL amber vial, an aliquot of 1.0 mL urine sample was diluted to a final volume of 20 mL by DI water and treated with 300 μL 100 ppm Mirex solution and 600 μL 2 M hydrochloric acid. The sample volume created no headspace in the vials. A commercially available Stir Bars (Twister™, 10 mm×1 mm, Gerstel, Mülheim an der Ruhr, Germany) was placed in the vial, and the solution was stirred for 2 hours at 1000 rpm. The stir bar was removed from the solution, rinsed with DI water, dried with lint free paper, and placed into a thermal desorption tube for GC-MS analysis.

Gas Chromatography Electron Ionization Mass Spectrometry qualitative and semi-quantitative analysis. VOCs from urine samples were analyzed by a thermal desorption unit, TDU (Gerstel), coupled with a 6890 GC system and a 5973 N Mass Selective Detector (Agilent Technologies, Wilmington, Del.). The initial TDU temperature was 45° C. After holding for 0.5 min, the temperature of TDU was increased to 300° C. at 60° C. $\min^{-1}$ and held for 5 min. Desorption gas flow was set at 1.0 mL $\min^{-1}$. During desorption, all the desorbed compounds were concentrated in a cold injection system, CIS-4 (Gerstel), at −40° C. prior to GC injection. Once the desorption process was completed, the CIS temperature was ramped to 300° C. at 12° C. $\sec^{-1}$ and held for 5 min in a solvent vent mode. Splitless mode was employed for the GC analysis. A ZB-5 ms capillary column (30 m×0.25 mm×0.25 μm with 5% phenyl-95% dimethylpolysiloxane, Phenomenex, USA) was used. The oven temperature was programmed as follows: held for 5 min at 35° C.; raised at 10° C. $\min^{-1}$ to 300° C.; and held for 10 min at 300° C. The VOCs in urine samples were detected by Mass Selective detector in scan mode (20-1000 m/z).

Data processing and statistical analysis. The identification of VOCs profile in urine samples was based on the National Institute of Standards and Technology (NIST) Library Search Report. The relative intensity of each peak was normalized against that of the internal standard, Mirex. The relative peak area ratio was used to do semi-quantitative analysis of VOCs in the statistical analysis.

Demographic information of each patients and the VOCs profiles including the relative peak area ratio of each sample were used in statistical analysis. The statistical significance of each VOC was tested by Wilcoxon test. With the cutoff p-values 0.05, the heat maps were plotted with those selected VOCs. Applying a liberal cutoff of 0.20 on the p-values, the logistic regression model was applied for further selection of significant VOCs. The significant VOCs (p-values <0.2) are cited in Table 5 and Table 6. The performance of those significant VOCs in differentiating PCa or cancer from controls was evaluated by cross-validation.

TABLE 3

List of significant VOCs mostly found in prostate negative control samples. All those VOCs were represented by Chemical Abstracts Service (CAS) number. Each CAS number is specific for each compound. P value (<0.2) of all those compounds were calculated from Wilcoxon rank sum test.

| Compound (CAS NO.) | P value | Occurrence in all patients |
|---|---|---|
| 000112-12-9 | 0.00068282 | 32 |
| 1000079-50-7 | 0.00102648 | 27 |
| 007726-08-1 | 0.00127984 | 20 |
| 006398-62-5 | 0.00314710 | 19 |
| 1000283-04-2 | 0.00403295 | 9 |
| 000109-21-7 | 0.00403295 | 9 |
| 018679-18-0 | 0.00711693 | 8 |
| 062016-76-6 | 0.00856683 | 11 |
| 000143-07-7 | 0.01111954 | 69 |
| 1000268-74-7 | 0.01197002 | 14 |
| 002867-20-1 | 0.01245789 | 7 |
| 055751-83-2 | 0.01346178 | 54 |
| 1000072-26-3 | 0.01544094 | 30 |
| 000106-44-5 | 0.01732229 | 13 |
| 000301-02-0 | 0.01761897 | 33 |
| 025693-00-9 | 0.02163627 | 10 |
| 002244-16-8 | 0.02167000 | 6 |
| 000921-47-1 | 0.02167000 | 6 |
| 000544-77-4 | 0.02167000 | 6 |
| 000111-84-2 | 0.02167000 | 6 |
| 000544-31-0 | 0.02483949 | 9 |
| 005210-12-8 | 0.02490783 | 12 |
| 000088-04-0 | 0.02536080 | 20 |
| 004748-78-1 | 0.02600387 | 12 |
| 002934-07-8 | 0.02600387 | 12 |
| 029899-13-6 | 0.02607898 | 9 |
| 019095-24-0 | 0.02661439 | 74 |
| 1000130-99-4 | 0.02737158 | 9 |
| 000606-43-9 | 0.02737158 | 9 |
| 000826-81-3 | 0.02832155 | 12 |
| 1000153-59-4 | 0.02839018 | 33 |
| 062736-78-1 | 0.02936950 | 15 |
| 074367-31-0 | 0.03310954 | 9 |
| 314283-74-4 | 0.03755050 | 5 |
| 1000296-68-0 | 0.03755050 | 5 |
| 1000099-92-9 | 0.03755050 | 5 |
| 099858-37-4 | 0.03755050 | 5 |
| 069140-09-6 | 0.03755050 | 5 |
| 053670-48-7 | 0.03755050 | 5 |
| 022539-72-6 | 0.03755050 | 5 |
| 017312-53-7 | 0.03755050 | 5 |
| 003638-33-3 | 0.03755050 | 5 |
| 001821-02-9 | 0.03755050 | 5 |
| 000207-84-1 | 0.03958176 | 20 |
| 1000189-14-9 | 0.04379901 | 8 |
| 1000131-33-2 | 0.04438730 | 17 |
| 040736-18-3 | 0.04946275 | 22 |
| 1000280-36-5 | 0.04964531 | 11 |
| 035320-23-1 | 0.05041537 | 8 |
| 001195-32-0 | 0.05049584 | 41 |
| 000095-75-0 | 0.05443974 | 17 |
| 103439-06-1 | 0.05527625 | 8 |
| 1000159-40-6 | 0.05784954 | 8 |
| 003508-78-9 | 0.05784954 | 8 |
| 001120-16-7 | 0.06126649 | 13 |
| 000194-59-2 | 0.06263131 | 21 |
| 1000281-77-4 | 0.06506294 | 4 |
| 1000259-58-5 | 0.06506294 | 4 |

TABLE 3-continued

List of significant VOCs mostly found in prostate negative control samples. All those VOCs were represented by Chemical Abstracts Service (CAS) number. Each CAS number is specific for each compound. P value (<0.2) of all those compounds were calculated from Wilcoxon rank sum test.

| Compound (CAS NO.) | P value | Occurrence in all patients |
|---|---|---|
| 1000252-56-5 | 0.06506294 | 4 |
| 1000193-81-2 | 0.06506294 | 4 |
| 1000191-14-6 | 0.06506294 | 4 |
| 1000147-85-5 | 0.06506294 | 4 |
| 1000122-21-1 | 0.06506294 | 4 |
| 1000079-52-1 | 0.06506294 | 4 |
| 058102-14-0 | 0.06506294 | 4 |
| 056438-07-4 | 0.06506294 | 4 |
| 054340-85-1 | 0.06506294 | 4 |
| 039890-45-4 | 0.06506294 | 4 |
| 024569-83-3 | 0.06506294 | 4 |
| 018803-29-7 | 0.06506294 | 4 |
| 016957-70-3 | 0.06506294 | 4 |
| 015450-84-7 | 0.06506294 | 4 |
| 007212-40-0 | 0.06506294 | 4 |
| 001560-95-8 | 0.06506294 | 4 |
| 001115-65-7 | 0.06506294 | 4 |
| 000815-57-6 | 0.06506294 | 4 |
| 000112-84-5 | 0.06506294 | 4 |
| 000099-49-0 | 0.06506294 | 4 |
| 000098-83-9 | 0.06506294 | 4 |
| 000097-87-0 | 0.06506294 | 4 |
| 000079-31-2 | 0.06506294 | 4 |
| 002305-36-4 | 0.06692430 | 29 |
| 004389-50-8 | 0.07061977 | 29 |
| 001552-42-7 | 0.07094097 | 24 |
| 001002-84-2 | 0.07123263 | 72 |
| 003386-33-2 | 0.07594316 | 42 |
| 1000292-49-0 | 0.07601219 | 10 |
| 000874-41-9 | 0.07649864 | 7 |
| 025246-27-9 | 0.08006905 | 7 |
| 000488-23-3 | 0.08006905 | 7 |
| 024851-98-7 | 0.08377371 | 7 |
| 018082-56-9 | 0.08428276 | 13 |
| 062016-79-9 | 0.08655667 | 15 |
| 000625-30-9 | 0.08688002 | 18 |
| 022818-69-5 | 0.08761594 | 7 |
| 006728-26-3 | 0.08761594 | 7 |
| 015677-71-1 | 0.08870757 | 10 |
| 003234-02-4 | 0.09159908 | 7 |
| 074420-82-9 | 0.09322775 | 40 |
| 077536-30-2 | 0.09572648 | 7 |
| 000123-95-5 | 0.09695469 | 32 |
| 001007-28-9 | 0.09721853 | 8 |
| 040710-42-7 | 0.10000144 | 7 |
| 024524-54-7 | 0.10000144 | 7 |
| 000705-86-2 | 0.10000144 | 7 |
| 000629-62-9 | 0.10470861 | 15 |
| 000112-79-8 | 0.10605858 | 23 |
| 000638-58-4 | 0.11127417 | 12 |
| 055282-12-7 | 0.11975568 | 18 |
| 000112-61-8 | 0.12134995 | 68 |
| 1000130-81-4 | 0.12168574 | 25 |
| 055299-24-6 | 0.12376097 | 21 |
| 001498-82-4 | 0.12394173 | 20 |
| 1000245-49-2 | 0.12398499 | 5 |
| 1000211-18-7 | 0.12398499 | 5 |
| 000931-56-6 | 0.12398499 | 5 |
| 052253-93-7 | 0.12773675 | 24 |
| 000104-67-6 | 0.12791795 | 25 |
| 020483-36-7 | 0.12903319 | 9 |
| 002078-13-9 | 0.12907044 | 39 |
| 017450-32-7 | 0.13080180 | 14 |
| 002216-51-5 | 0.13249300 | 6 |
| 000544-63-8 | 0.13266939 | 75 |
| 065598-01-8 | 0.13483874 | 14 |
| 000112-80-1 | 0.13661450 | 62 |
| 000142-60-9 | 0.13841439 | 6 |
| 106833-31-2 | 0.13871471 | 17 |
| 010229-10-4 | 0.13881640 | 9 |
| 003555-47-3 | 0.14031917 | 68 |
| 1000281-96-8 | 0.14232801 | 62 |

TABLE 3-continued

List of significant VOCs mostly found in prostate negative control samples. All those VOCs were represented by Chemical Abstracts Service (CAS) number. Each CAS number is specific for each compound. P value (<0.2) of all those compounds were calculated from Wilcoxon rank sum test.

| Compound (CAS NO.) | P value | Occurrence in all patients |
| --- | --- | --- |
| 041406-00-2 | 0.14391754 | 9 |
| 005762-56-1 | 0.14391754 | 9 |
| 1000130-81-0 | 0.14453762 | 6 |
| 1000282-99-1 | 0.14528559 | 20 |
| 156785-76-1 | 0.14703896 | 39 |
| 156785-69-2 | 0.14744081 | 22 |
| 282104-35-2 | 0.15052381 | 37 |
| 1000194-27-6 | 0.15086632 | 6 |
| 007408-81-3 | 0.15086632 | 6 |
| 001477-63-0 | 0.15740405 | 6 |
| 001758-88-9 | 0.15741634 | 19 |
| 005129-56-6 | 0.15963712 | 36 |
| 073420-26-5 | 0.16008428 | 9 |
| 002319-29-1 | 0.16415425 | 6 |
| 022378-50-3 | 0.16939077 | 16 |
| 055449-66-6 | 0.17067747 | 14 |
| 022058-71-5 | 0.17160157 | 9 |
| 145344-72-5 | 0.17389531 | 39 |
| 122085-61-4 | 0.18116796 | 49 |
| 007476-79-1 | 0.18294830 | 11 |
| 004097-88-5 | 0.18365124 | 16 |
| 000295-17-0 | 0.18402561 | 62 |
| 195194-80-0 | 0.18667768 | 53 |
| 002305-05-7 | 0.18869929 | 11 |
| 006259-76-3 | 0.19389282 | 17 |
| 000124-10-7 | 0.19401148 | 13 |
| 000104-50-7 | 0.19458252 | 11 |

TABLE 4

List of significant VOCs mostly found in prostate cancer samples. All those VOCs were represented by Chemical Abstracts Service (CAS) number. Each CAS number is specific for each compound. P value (<0.2) of all those compounds were calculated from Wilcoxon rank sum test.

| Compound (CAS No.) | P value | Occurrence in all patients |
| --- | --- | --- |
| 026537-06-4 | 0.00256512 | 7 |
| 100872-42-2 | 0.00558572 | 6 |
| 066358-25-6 | 0.00558572 | 6 |
| 000078-83-1 | 0.00674394 | 19 |
| 046498-17-3 | 0.00766180 | 16 |
| 000694-87-1 | 0.00957440 | 19 |
| 1000150-37-1 | 0.01132765 | 8 |
| 035953-53-8 | 0.01163461 | 20 |
| 1000224-74-2 | 0.01205805 | 5 |
| 033622-26-3 | 0.01205805 | 5 |
| 021504-04-1 | 0.01205805 | 5 |
| 005009-32-5 | 0.01205805 | 5 |
| 037148-64-4 | 0.01302171 | 15 |
| 032703-82-5 | 0.01416795 | 8 |
| 000593-49-7 | 0.01657831 | 13 |
| 017983-71-0 | 0.01899222 | 24 |
| 1000274-60-9 | 0.01976216 | 15 |
| 003282-18-6 | 0.02120933 | 20 |
| 000295-48-7 | 0.02361339 | 38 |
| 1000282-06-8 | 0.02591682 | 4 |
| 1000254-68-4 | 0.02591682 | 4 |
| 058417-83-7 | 0.02591682 | 4 |
| 025379-26-4 | 0.02591682 | 4 |
| 004316-48-7 | 0.02591682 | 4 |
| 003221-61-2 | 0.02591682 | 4 |
| 001758-85-6 | 0.02591682 | 4 |
| 000085-69-8 | 0.02591682 | 4 |
| 002245-38-7 | 0.02609732 | 7 |
| 017995-44-7 | 0.02813447 | 35 |
| 000120-53-6 | 0.03065695 | 7 |
| 1000079-56-3 | 0.03257790 | 14 |
| 055429-13-5 | 0.03785746 | 48 |
| 040426-44-6 | 0.03828762 | 20 |
| 1000190-13-7 | 0.03838471 | 39 |
| 097371-50-1 | 0.04170304 | 9 |
| 000761-65-9 | 0.04430159 | 47 |
| 000589-92-4 | 0.04563443 | 9 |
| 000107-68-6 | 0.04766953 | 11 |
| 088017-34-9 | 0.05037365 | 6 |
| 1000103-29-8 | 0.05218215 | 42 |
| 1000190-57-6 | 0.05593600 | 6 |
| 000995-82-4 | 0.05593911 | 67 |
| 069833-43-8 | 0.05890359 | 6 |
| 003782-85-2 | 0.05950010 | 52 |
| 023933-57-5 | 0.06052164 | 8 |
| 006946-24-3 | 0.06121013 | 22 |
| 000775-54-2 | 0.06126649 | 13 |
| 101100-38-3 | 0.06195226 | 20 |
| 001472-09-9 | 0.06200073 | 6 |
| 000142-96-1 | 0.06200073 | 6 |
| 000112-95-8 | 0.06253428 | 73 |
| 000629-78-7 | 0.06287611 | 64 |
| 131758-71-9 | 0.06548380 | 11 |
| 074339-51-8 | 0.07225223 | 8 |
| 000116-09-6 | 0.07291959 | 33 |
| 000995-83-5 | 0.07331041 | 40 |
| 068595-79-9 | 0.07815932 | 14 |
| 004182-41-6 | 0.07903807 | 10 |
| 024535-53-3 | 0.08016577 | 44 |
| 000629-99-2 | 0.08084398 | 14 |
| 018163-06-9 | 0.08222156 | 8 |
| 027869-56-3 | 0.08285921 | 28 |
| 000100-51-6 | 0.08410302 | 17 |
| 013754-10-4 | 0.08654393 | 23 |
| 1000258-63-4 | 0.08674117 | 17 |
| 000095-73-8 | 0.08741033 | 12 |
| 004765-59-7 | 0.08946725 | 8 |
| 110028-10-9 | 0.09327829 | 8 |
| 074299-38-0 | 0.09376392 | 12 |
| 002941-78-8 | 0.09386824 | 58 |
| 000934-80-5 | 0.09541056 | 14 |
| 1000071-69-6 | 0.09930852 | 10 |
| 1000283-54-9 | 0.10048268 | 12 |
| 1000264-16-7 | 0.10048268 | 12 |
| 007492-70-8 | 0.10129071 | 8 |
| 077509-04-7 | 0.10169130 | 5 |
| 061142-53-8 | 0.10169130 | 5 |
| 030012-51-2 | 0.10169130 | 5 |
| 029281-39-8 | 0.10169130 | 5 |
| 007429-44-9 | 0.10169130 | 5 |
| 1000187-10-6 | 0.10694088 | 5 |
| 007206-25-9 | 0.10694088 | 5 |
| 000630-04-6 | 0.10757973 | 12 |
| 000052-01-7 | 0.11200734 | 14 |
| 005202-36-8 | 0.11334001 | 72 |
| 015356-70-4 | 0.11423006 | 20 |
| 000605-45-8 | 0.11498845 | 10 |
| 001860-39-5 | 0.11558514 | 14 |
| 302604-54-2 | 0.11808260 | 5 |
| 052988-92-8 | 0.11808260 | 5 |
| 025973-55-1 | 0.11808260 | 5 |
| 002142-04-3 | 0.11808260 | 5 |
| 001459-93-4 | 0.11808260 | 5 |
| 000502-69-2 | 0.11865998 | 25 |
| 155670-84-1 | 0.12398499 | 5 |
| 1000159-39-1 | 0.12398499 | 5 |
| 1000130-81-2 | 0.12398499 | 5 |
| 088454-93-7 | 0.12398499 | 5 |
| 055124-79-3 | 0.12398499 | 5 |
| 000761-35-3 | 0.12398499 | 5 |
| 000124-17-4 | 0.12398499 | 5 |
| 005399-02-0 | 0.12706195 | 12 |
| 058263-56-2 | 0.13265336 | 53 |

TABLE 4-continued

List of significant VOCs mostly found in prostate cancer samples.
All those VOCs were represented by Chemical Abstracts Service (CAS)
number. Each CAS number is specific for each compound. P value ($<0.2$)
of all those compounds were calculated from Wilcoxon rank sum test.

| Compound (CAS No.) | P value | Occurrence in all patients |
|---|---|---|
| 029427-58-5 | 0.13433285 | 7 |
| 1000161-94-5 | 0.13558376 | 12 |
| 018748-91-9 | 0.13897131 | 14 |
| 000090-05-1 | 0.13990512 | 7 |
| 1000245-69-5 | 0.14565358 | 7 |
| 017312-80-0 | 0.14565358 | 7 |
| 013360-61-7 | 0.14718449 | 27 |
| 1000221-77-6 | 0.15158114 | 7 |
| 000692-24-0 | 0.15454944 | 9 |
| 072088-09-6 | 0.15654700 | 15 |
| 000629-79-8 | 0.16166024 | 18 |
| 108904-53-6 | 0.16398499 | 7 |
| 058668-40-9 | 0.16398499 | 7 |
| 063673-76-7 | 0.16485895 | 72 |
| 309742-44-7 | 0.16774860 | 13 |
| 004423-10-3 | 0.17046677 | 7 |
| 325728-88-9 | 0.17466875 | 56 |
| 000713-46-2 | 0.17713862 | 7 |
| 104255-99-4 | 0.17758779 | 9 |
| 000927-55-9 | 0.18342213 | 24 |
| 1000265-59-5 | 0.18400308 | 7 |
| 000588-06-7 | 0.18400308 | 7 |
| 309735-29-3 | 0.18402341 | 18 |
| 1000098-14-8 | 0.18413800 | 30 |
| 074299-32-4 | 0.18574402 | 19 |
| 004209-22-7 | 0.19002435 | 9 |
| 007206-21-5 | 0.19041732 | 19 |
| 1000267-28-6 | 0.19468149 | 40 |
| 000295-02-3 | 0.19633505 | 30 |
| 1000287-50-5 | 0.19647808 | 9 |
| 098640-29-0 | 0.19960807 | 13 |

Example 2

Additional Studies of Volatile Organic Compounds in Urine of Prostate Cancer Patients A. Patient Demographics

TABLE 5

Demographics for patients in urinary VOCs study of prostate cancer

| | Status | Number | Age | Race |
|---|---|---|---|---|
| Controls (Ctrl)* | No prostate related health issue | 6 | 53.5 ± 12.3 | White |
| Prostate cancer (PC) | TRUS Positive | 12 | 65.1 ± 7.3 | White |
| Prostate cancer-negative (PCN) | TRUS Negative | 9 | 68.2 ± 9.6 | White |

*Control samples were collected randomly from patients whose medical visits were not prostate problem related.

Sample storage: Urine Samples from patients were centrifuged at 300 g for 10 min. The supernatant was separated and kept at −80° C. until analysis.

Stir Bar Sorptive Extraction (SBSE): Extraction of VOCs was performed by SBSE followed by thermal desorption coupled with Gas Chromatography/Mass spectrometry (GC/MS). Into a 20 ml glass vial, 1 ml urine was diluted in DI water to reach a final volume of 20 mL. The urine solution was then acidified with 600 μl of 2M HCl and 300 μl of 1 ppm Mirex were added as the internal standard. A stir bar coated with PDMS (Twister™, 10 mm×1 mm, 169 Gerstel, Mülheim an der Ruhr, Germany) was placed into the solution, and stirred for 2 hours at 1000 rpm. The stir bar was then removed from the solution, rinsed with DI water, dried with lint free paper, and placed into a thermal desorption tube for GC-MS analysis.

Thermal Desorption-GC/MS detection. A thermal desorption unit, TDU (Gerstel), coupled with a 6890 GC system and a 5973 N Mass Selective Detector (Agilent Technologies, Wilmington, Del.) was used to analyze VOCs.

Data processing method. ChemStation was used for data analysis and VOCs were identified by NIST mass spectra database. Preliminary data was acquired through the significant occurrence analysis of the VOCs in each sample. Pivot Table were processed to analyze the occurrence of each VOC. Specific VOC metabolites with significant occurrence were listed in this preliminary report as potential biomarker for prostate cancer diagnosis.

Results. A total of 1,612 different VOCs detected in all prostate cancer positive, negative, and control samples. Among those VOCs, 41 VOCs were found to be in prostate cancer positive urine samples only; 3 were in prostate cancer negative samples only; and 10 were in control samples only. The compounds are selected based on their occurrence in the samples of specific category (i.e. PC, PCN, and Ctrl) more than twice. In addition, some VOCs were found with higher occurrence in one category than others. 38 VOCs were mostly found in prostate cancer positive urine samples; 5 were mostly in prostate cancer negative samples; and 34 were mostly in control samples. The significant VOCs are cited in Table 6, Table 7, Table 8 and Table 9.

TABLE 6

Significant VOCs distributions in prostate cancer, prostate cancer-negative, and control samples

| | Significant VOCs Distributions (No. of compounds) | |
|---|---|---|
| Samples | Only Appearing | Most Appearing |
| Controls | 10 | 34 |

VOCs found in controls only

| | | |
|---|---|---|
| 2-Hexene, 3-methyl-, (Z)- | 4-Methyldocosane | Phthalane |
| 2-Nonenal, (E)- | Acetic acid, hydrazide | Propenone, 3-(2-benzoxazolylthio)-1-phenyl- |
| 2-Pentenoic acid, 4-methyl-, methyl ester | Estra-1,3,5(10)-trien-17-one, 11-hydroxy-3-methoxy-, (11.alpha.)- | |

TABLE 6-continued

Significant VOCs distributions in prostate cancer,
prostate cancer-negative, and control samples

| Samples | Significant VOCs Distributions (No. of compounds) | |
|---|---|---|
| | Only Appearing | Most Appearing |
| 3-Hexadecene, (Z)- | Morpholine, 4-phenyl- | |
| Prostate cancer | 41 | 38 |
| VOCs found in Prostate cancer only | | |
| 2,2'-Bi-1,3-dioxolane, 2-phenyl- | 2,5-Furandione, 3,4-dimethyl- | Estra-1,3,5(10)-trien-17-one, 2-methoxy-3-[(trimethylsilyl)oxy]-, O-methyloxime |
| 2,5-Furandione, 3-methyl-4-propyl- | 4-(Dichloromethyl)-5-hydroxy-2(3H,5H)-furanone | Heneicosane |
| 3-(6-Methyl-3-pyridyl)-1,5-di(p-tolyl)-2-pyrazoline | 4-Octynoic acid, 7-(t-butyldimethylsilyloxy)-, t-butyldimethylsilyl ester | Methanesulfonic acid, thio-, S-[[[[(methylsulfinyl)methyl]thio]methoxy] methyl] ester |
| 4-Bromo-2,5-dimethoxyamphetamine | 5-[1,4-Dioxa-8-azaspiro[4.5]dec-8-yl]-6-ethyl-2,4(1H,3H)-pyrimidinedion | Methyl (5-hydroxy-1H-benzimidazol-2-yl)carbamate |
| Benzene, 4-ethyl-1,2-dimethyl- | 5H-Naphtho[2,3-c]carbazole, 5-methyl- | Methyl 8-oxooctanoate |
| Nonahexacontanoic acid | 7-Acetyl-6-ethyl-1,1,4,4-tetramethyltetralin | Phenol, 2-(1,1-dimethylethyl)- |
| Thiocyanic acid carbazol-3,6-diylester | Acetamide, N-(4-chlorophenyl)-N-methoxy- | Prasterone-3-sulfate |
| Trimethylsilyl fluoride | Benzene, 1,1'-cyclopropylidenebis- | Semioxamazide |
| 1,3,2-Oxazaborolane, 2-butyl- | Benzene, 1,2-dichloro-3-methyl- | Sorbic Acid |
| 1-Adamantanecarboxylic acid, 2-propenyl ester | Benzonitrile, 2-methyl- | Spiro[2,4,5,6,7,7a-hexahydro-2-oxo-4,4,7a-trimethylbenzofuran]-7,2'-(oxirane) |
| 1-Adamantanemethylamine, .alpha.-methyl- | Butane, 2-(ethenyloxy)-2-methyl- | Tridecane, 6-methyl- |
| 1-Docosanethiol | Cyclohexanol, 5-methyl-2-(1-methylethyl)-, [1S-(1.alpha., 2.beta., 5.beta.)]- | |
| 1-Methoxy-1-buten-3-yne | Cyclohexanone | |
| 1-Propanol, 2-methyl- | Cyclohexanone, 5-methyl-2-(1-methylethyl)-, trans- | |
| 2(1H)-Naphthalenone, octahydro-1,1,4a-trimethyl-, trans- | erythro-9,10-Dibromopentacosane | |
| Prostate cancer-negative | 3 | 5 |
| VOCs found in Prostate cancer-negative only | | |
| Formic acid, 1-(4,7-dihydro-2-methyl-7-oxopyrazolo[1,5-a]pyrimidin-5-yl)-, methyl ester | .alpha.-Methylstyrene | Benzenamine, 4-bromo-3-chloro-N-(4-methylthiobenzylydene)- |

TABLE 7

List of significant VOCs mostly found in control samples. "PC" represents
prostate cancer samples; "PCN" represents prostate cancer-negative
samples; "Ctrl" represents control samples; "DI" represent deionized water sample.

| | Occurrence | | | | Occurrence Rate (%) | | |
|---|---|---|---|---|---|---|---|
| Compounds | PC (n = 12) | PCN (n = 9) | Ctrl (n = 6) | DI | PC | PCN | Ctrl |
| 2-Hexene, 3-methyl-, (Z)- | 0 | 0 | 2 | 0 | 0.0 | 0.0 | 33.3 |
| 2-Nonenal, (E)- | 0 | 0 | 2 | 0 | 0.0 | 0.0 | 33.3 |
| 2-Pentenoic acid, 4-methyl-, methyl ester | 0 | 0 | 2 | 0 | 0.0 | 0.0 | 33.3 |
| 3-Hexadecene, (Z)- | 0 | 0 | 2 | 0 | 0.0 | 0.0 | 33.3 |

TABLE 7-continued

List of significant VOCs mostly found in control samples. "PC" represents prostate cancer samples; "PCN" represents prostate cancer-negative samples; "Ctrl" represents control samples; "DI" represent deionized water sample.

| | Occurrence | | | | Occurrence Rate (%) | | |
|---|---|---|---|---|---|---|---|
| | PC | PCN | Ctrl | | PC | PCN | Ctrl |
| Compounds | (n = 12) | (n = 9) | (n = 6) | DI | | | |
| 4-Methyldocosane | 0 | 0 | 2 | 0 | 0.0 | 0.0 | 33.3 |
| Acetic acid, hydrazide | 0 | 0 | 2 | 0 | 0.0 | 0.0 | 33.3 |
| Estra-1,3,5(10)-trien-17-one, 11-hydroxy-3-methoxy-, (11•alpha•)- | 0 | 0 | 2 | 0 | 0.0 | 0.0 | 33.3 |
| Morpholine, 4-phenyl- | 0 | 0 | 2 | 0 | 0.0 | 0.0 | 33.3 |
| Phthalan | 0 | 0 | 2 | 0 | 0.0 | 0.0 | 33.3 |
| Propenone, 3-(2-benzoxazolylthio)-1-phenyl- | 0 | 0 | 2 | 0 | 0.0 | 0.0 | 33.3 |
| Naphthalene | 0 | 1 | 3 | 0 | 0.0 | 11.1 | 50.0 |
| Naphthalene, 1,2,3,4-tetrahydro-1,6-dimethyl-4-(1-methylethyl)-, (1S-cis)- | 0 | 1 | 3 | 0 | 0.0 | 11.1 | 50.0 |
| 9-Octadecenamide, (Z)- | 0 | 1 | 2 | 0 | 0.0 | 11.1 | 33.3 |
| Isoindole-1,3(1H,3H)-dione, 5-benzoyl-2-(4-methylphenyl)- | 0 | 1 | 2 | 0 | 0.0 | 11.1 | 33.3 |
| Decanamide, N-(2-hydroxyethyl)- | 0 | 2 | 4 | 0 | 0.0 | 22.2 | 66.7 |
| Indole | 0 | 2 | 2 | 0 | 0.0 | 22.2 | 33.3 |
| 2-Undecanone | 0 | 3 | 5 | 0 | 0.0 | 33.3 | 83.3 |
| 2(3H)-Furanone, 5-heptyldihydro- | 0 | 3 | 4 | 0 | 0.0 | 33.3 | 66.7 |
| 5-Octadecene, (E)- | 1 | 0 | 2 | 0 | 8.3 | 0.0 | 33.3 |
| Acetamide, N-9-phenanthrenyl- | 1 | 0 | 2 | 0 | 8.3 | 0.0 | 33.3 |
| Dibenz[a,c]cycloheptan-9-amine, 2,3,4-trimethoxy-N-acetyl- | 1 | 0 | 2 | 0 | 8.3 | 0.0 | 33.3 |
| 1,3,5,7,9-Pentaethylcyclopentasiloxane | 1 | 1 | 3 | 0 | 8.3 | 11.1 | 50.0 |
| 3-(Benzylthio)acrylic acid, methyl ester | 1 | 1 | 2 | 0 | 8.3 | 11.1 | 33.3 |
| 3,6-Dioxa-2,4,5,7-tetrasilaoctane, 2,2,4,4,5,5,7,7-octamethyl- | 1 | 1 | 2 | 0 | 8.3 | 11.1 | 33.3 |
| 4H-1,2,4-Triazole-3-thiol, 4-allyl-5-(1-naphthylmethyl)- | 1 | 1 | 2 | 0 | 8.3 | 11.1 | 33.3 |
| Cobaltocene, 1,1'-diphenyl- | 1 | 1 | 2 | 0 | 8.3 | 11.1 | 33.3 |
| Cyclohexene, 1-methyl-4-(1-methylethylidene)- | 1 | 1 | 2 | 0 | 8.3 | 11.1 | 33.3 |
| Cyclopentadecane | 1 | 1 | 2 | 0 | 8.3 | 11.1 | 33.3 |
| Phosphine oxide, bis(pentamethylphenyl)- | 1 | 1 | 2 | 0 | 8.3 | 11.1 | 33.3 |
| trans-2,3-Methylenedioxy-b-methyl-b-nitrostyrene | 1 | 1 | 2 | 0 | 8.3 | 11.1 | 33.3 |
| 7-Methyl-Z-tetradecen-1-ol acetate | 1 | 2 | 2 | 0 | 8.3 | 22.2 | 33.3 |
| Androst-5,16-diene-3•beta•-ol | 1 | 2 | 2 | 0 | 8.3 | 22.2 | 33.3 |
| 4-(4-Chlorophenyl)-2,6-diphenylpyridine | 1 | 4 | 3 | 0 | 8.3 | 44.4 | 50.0 |
| Oxirane, hexadecyl- | 2 | 0 | 3 | 0 | 16.7 | 0.0 | 50.0 |
| 4(1H)-Pyrimidinone, 2,6-diamino- | 2 | 1 | 2 | 0 | 16.7 | 11.1 | 33.3 |
| 7H-Dibenzo[b,g]carbazole, 7-methyl | 2 | 1 | 2 | 0 | 16.7 | 11.1 | 33.3 |
| dl-•alpha•-(Methylaminomethyl)benzyl alcohol | 2 | 1 | 2 | 0 | 16.7 | 11.1 | 33.3 |
| Ethanol, 2-(methylamino)- | 2 | 1 | 2 | 0 | 16.7 | 11.1 | 33.3 |
| Hexadecane | 3 | 2 | 5 | 0 | 25.0 | 22.2 | 83.3 |
| Isopropyl Palmitate | 3 | 2 | 3 | 0 | 25.0 | 22.2 | 50.0 |
| Formamide, N,N-diethyl- | 4 | 1 | 4 | 0 | 33.3 | 11.1 | 66.7 |
| Undecanoic acid, 10-methyl-, methyl ester | 4 | 3 | 5 | 0 | 33.3 | 33.3 | 83.3 |

TABLE 7-continued

List of significant VOCs mostly found in control samples. "PC" represents
prostate cancer samples; "PCN" represents prostate cancer-negative
samples; "Ctrl" represents control samples; "DI" represent deionized water sample.

| | Occurrence | | | | Occurrence Rate (%) | | |
|---|---|---|---|---|---|---|---|
| Compounds | PC (n = 12) | PCN (n = 9) | Ctrl (n = 6) | DI | PC | PCN | Ctrl |
| Octadecane, 1-chloro- | 5 | 4 | 6 | 0 | 41.7 | 44.4 | 100.0 |
| Propanoic acid, 2-methyl-, 1-(1,1-dimethylethyl)-2-methyl-1,3-propanediyl ester | 6 | 3 | 6 | 0 | 50.0 | 33.3 | 100.0 |

TABLE 8

List of significant VOCs mostly found in prostate cancer samples. "PC"
represents prostate cancer samples; "PCN" represents prostate
cancer-negative samples; "Ctrl" represents control samples;
"DI" represent deionized water sample.

| | Occurrence | | | | Occurrence Rate (%) | | |
|---|---|---|---|---|---|---|---|
| Compounds | PC (n = 12) | PCN (n = 9) | Ctrl (n = 6) | DI | PC | PCN | Ctrl |
| 2,2'-Bi-1,3-dioxolane, 2-phenyl- | 4 | 0 | 0 | 0 | 33.3 | 0.0 | 0.0 |
| 2,5-Furandione, 3-methyl-4-propyl- | 3 | 0 | 0 | 0 | 25.0 | 0.0 | 0.0 |
| 3-(6-Methyl-3-pyridyl)-1,5-di(p-tolyl)-2-pyrazoline | 3 | 0 | 0 | 0 | 25.0 | 0.0 | 0.0 |
| 4-Bromo-2,5-dimethoxyamphetamine | 3 | 0 | 0 | 0 | 25.0 | 0.0 | 0.0 |
| Benzene, 4-ethyl-1,2-dimethyl- | 3 | 0 | 0 | 0 | 25.0 | 0.0 | 0.0 |
| Nonahexacontanoic acid | 3 | 0 | 0 | 0 | 25.0 | 0.0 | 0.0 |
| Thiocyanic acid carbazol-3,6-diylester | 3 | 0 | 0 | 0 | 25.0 | 0.0 | 0.0 |
| Trimethylsilyl fluoride | 3 | 0 | 0 | 0 | 25.0 | 0.0 | 0.0 |
| 1,3,2-Oxazaborolane, 2-butyl- | 2 | 0 | 0 | 0 | 16.7 | 0.0 | 0.0 |
| 1-Adamantanecarboxylic acid, 2-propenyl ester | 2 | 0 | 0 | 0 | 16.7 | 0.0 | 0.0 |
| 1-Adamantanemethyl-amine, •alpha•-methyl- | 2 | 0 | 0 | 0 | 16.7 | 0.0 | 0.0 |
| 1-Docosanethiol | 2 | 0 | 0 | 0 | 16.7 | 0.0 | 0.0 |
| 1-Methoxy-1-buten-3-yne | 2 | 0 | 0 | 0 | 16.7 | 0.0 | 0.0 |
| 1-Propanol, 2-methyl- | 2 | 0 | 0 | 0 | 16.7 | 0.0 | 0.0 |
| 2(1H)-Naphthalenone, octahydro-1,1,4a-trimethyl-, trans- | 2 | 0 | 0 | 0 | 16.7 | 0.0 | 0.0 |
| 2,5-Furandione, 3,4-dimethyl- | 2 | 0 | 0 | 0 | 16.7 | 0.0 | 0.0 |
| 4-(Dichloromethyl)-5-hydroxy-2(3H,5H)-furanone | 2 | 0 | 0 | 0 | 16.7 | 0.0 | 0.0 |
| 4-Octynoic acid, 7-(t-butyldimethylsilyloxy)-, t-butyldimethylsilyl ester | 2 | 0 | 0 | 0 | 16.7 | 0.0 | 0.0 |
| 5-[1,4-Dioxa-8-azaspiro[4.5]dec-8-yl]-6-ethyl-2,4(1H,3H)-pyrimidinedion | 2 | 0 | 0 | 0 | 16.7 | 0.0 | 0.0 |
| 5H-Naphtho[2,3-c]carbazole, 5-methyl- | 2 | 0 | 0 | 0 | 16.7 | 0.0 | 0.0 |
| 7-Acetyl-6-ethyl-1,1,4,4-tetramethyltetralin | 2 | 0 | 0 | 0 | 16.7 | 0.0 | 0.0 |
| Acetamide, N-(4-chlorophenyl)-N-methoxy- | 2 | 0 | 0 | 0 | 16.7 | 0.0 | 0.0 |
| Benzene, 1,1'-cyclopropylidenebis- | 2 | 0 | 0 | 0 | 16.7 | 0.0 | 0.0 |

TABLE 8-continued

List of significant VOCs mostly found in prostate cancer samples. "PC" represents prostate cancer samples; "PCN" represents prostate cancer-negative samples; "Ctrl" represents control samples; "DI" represent deionized water sample.

| | Occurrence | | | | Occurrence Rate (%) | | |
|---|---|---|---|---|---|---|---|
| | PC | PCN | Ctrl | | | | |
| Compounds | (n = 12) | (n = 9) | (n = 6) | DI | PC | PCN | Ctrl |
| Benzene, 1,2-dichloro-3-methyl- | 2 | 0 | 0 | 0 | 16.7 | 0.0 | 0.0 |
| Benzonitrile, 2-methyl- | 2 | 0 | 0 | 0 | 16.7 | 0.0 | 0.0 |
| Butane, 2-(ethenyloxy)-2-methyl- | 2 | 0 | 0 | 0 | 16.7 | 0.0 | 0.0 |
| Cyclohexanol, 5-methyl-2-(1-methylethyl)-, [1S-(1•alpha•,2•beta•,5•beta•)]- | 2 | 0 | 0 | 0 | 16.7 | 0.0 | 0.0 |
| Cyclohexanone | 2 | 0 | 0 | 0 | 16.7 | 0.0 | 0.0 |
| Cyclohexanone, 5-methyl-2-(1-methylethyl)-, trans- | 2 | 0 | 0 | 0 | 16.7 | 0.0 | 0.0 |
| erythro-9,10-Dibromopentacosane | 2 | 0 | 0 | 0 | 16.7 | 0.0 | 0.0 |
| Estra-1,3,5(10)-trien-17-one, 2-methoxy-3-[(trimethylsilyl)oxy]-, O-methyloxime | 2 | 0 | 0 | 0 | 16.7 | 0.0 | 0.0 |
| Heneicosane | 2 | 0 | 0 | 0 | 16.7 | 0.0 | 0.0 |
| Methanesulfonic acid, thio-, S-[[[[(methylsulfinyl)methyl]thio]methoxy]methyl] ester | 2 | 0 | 0 | 0 | 16.7 | 0.0 | 0.0 |
| Methyl (5-hydroxy-1H-benzimidazol-2-yl)carbamate | 2 | 0 | 0 | 0 | 16.7 | 0.0 | 0.0 |
| Methyl 8-oxooctanoate | 2 | 0 | 0 | 0 | 16.7 | 0.0 | 0.0 |
| Phenol, 2-(1,1-dimethylethyl)- | 2 | 0 | 0 | 0 | 16.7 | 0.0 | 0.0 |
| Prasterone-3-sulfate | 2 | 0 | 0 | 0 | 16.7 | 0.0 | 0.0 |
| Semioxamazide | 2 | 0 | 0 | 0 | 16.7 | 0.0 | 0.0 |
| Sorbic Acid | 2 | 0 | 0 | 0 | 16.7 | 0.0 | 0.0 |
| Spiro[2,4,5,6,7,7a-hexahydro-2-oxo-4,4,7a-trimethylbenzofuran]-7,2'-(oxirane) | 2 | 0 | 0 | 0 | 16.7 | 0.0 | 0.0 |
| Tridecane, 6-methyl- | 2 | 0 | 0 | 0 | 16.7 | 0.0 | 0.0 |
| 2-Methoxy-2-methylbut-3-ene | 5 | 1 | 0 | 0 | 41.7 | 11.1 | 0.0 |
| (2,3-Diphenylcyclopropyl)methyl phenyl sulfoxide, trans- | 4 | 1 | 0 | 0 | 33.3 | 11.1 | 0.0 |
| Acetic acid, [(aminocarbonyl)amino]oxo- | 4 | 1 | 0 | 0 | 33.3 | 11.1 | 0.0 |
| Cyclotridecane | 4 | 1 | 0 | 0 | 33.3 | 11.1 | 0.0 |
| 2-[(4-Chloro-•alpha•-methylbenzylidene)hydrazino]-4-morpholino-6-(1-pyrrolidinyl)-1,3,5-triazine | 3 | 1 | 0 | 0 | 25.0 | 11.1 | 0.0 |
| Heptanoic acid, 2-methyl-2-butyl ester | 3 | 1 | 0 | 0 | 25.0 | 11.1 | 0.0 |
| 1-(5-Bicyclo[2.2.1]heptyl)ethylamine | 4 | 2 | 0 | 0 | 33.3 | 22.2 | 0.0 |
| 2,5-di-tert-Butyl-1,4-benzoquinone | 4 | 2 | 0 | 0 | 33.3 | 22.2 | 0.0 |
| Naphthalene, 1,6-dimethyl-4-(1-methylethyl)- | 4 | 2 | 0 | 0 | 33.3 | 22.2 | 0.0 |
| 1,3-Propanediamine, N-methyl- | 3 | 2 | 0 | 0 | 25.0 | 22.2 | 0.0 |
| 2-Amino-1-(o-methoxyphenyl)propane | 3 | 2 | 0 | 0 | 25.0 | 22.2 | 0.0 |

TABLE 8-continued

List of significant VOCs mostly found in prostate cancer samples. "PC" represents prostate cancer samples; "PCN" represents prostate cancer-negative samples; "Ctrl" represents control samples; "DI" represent deionized water sample.

| | Occurrence | | | | Occurrence Rate (%) | | |
|---|---|---|---|---|---|---|---|
| Compounds | PC (n = 12) | PCN (n = 9) | Ctrl (n = 6) | DI | PC | PCN | Ctrl |
| 2-Methoxy-4-vinylphenol | 5 | 3 | 0 | 0 | 41.7 | 33.3 | 0.0 |
| Pentasiloxane, 1,1,3,3,5,5,7,7,9,9-decamethyl- | 5 | 0 | 1 | 0 | 41.7 | 0.0 | 16.7 |
| 1,3,5,7-Cyclooctatetraene | 4 | 0 | 1 | 0 | 33.3 | 0.0 | 16.7 |
| Cyclohexanol, 5-methyl-2-(1-methylethyl)-, (1•alpha•,2•beta•,5•alpha•)-(•+/−•)- | 4 | 0 | 1 | 0 | 33.3 | 0.0 | 16.7 |
| Cyclotetradecane, 1,7,11-trimethyl-4-(1-methylethyl)- | 3 | 0 | 1 | 0 | 25.0 | 0.0 | 16.7 |
| Isolongifolene, 9,10-dehydro- | 3 | 0 | 1 | 0 | 25.0 | 0.0 | 16.7 |
| Metacetamol | 3 | 0 | 1 | 0 | 25.0 | 0.0 | 16.7 |
| Octadecanoic acid, tert-butyldimethylsilyl ester | 3 | 0 | 1 | 0 | 25.0 | 0.0 | 16.7 |
| Hexadecane, 1-chloro- | 5 | 1 | 1 | 0 | 41.7 | 11.1 | 16.7 |
| Trisiloxane, 1,1,1,5,5,5-hexamethyl-3,3-bis[(trimethylsilyl)oxy]- | 5 | 1 | 1 | 0 | 41.7 | 11.1 | 16.7 |
| Hexasiloxane, tetradecamethyl- | 3 | 1 | 1 | 0 | 25.0 | 11.1 | 16.7 |
| Levoglucosenone | 3 | 1 | 1 | 0 | 25.0 | 11.1 | 16.7 |
| Silane, 1,4-phenylenebis[trimethyl | 3 | 1 | 1 | 0 | 25.0 | 11.1 | 16.7 |
| Z-8-Hexadecene | 3 | 1 | 1 | 0 | 25.0 | 11.1 | 16.7 |
| Ether, bis(p-tert-butylphenyl) | 6 | 2 | 1 | 0 | 50.0 | 22.2 | 16.7 |
| 2-Heptanamine, 5-methyl- | 5 | 2 | 1 | 0 | 41.7 | 22.2 | 16.7 |
| 1,1,1,3,5,7,9,11,11,11-Decamethyl-5-(trimethylsiloxy)hexasiloxane | 3 | 2 | 1 | 0 | 25.0 | 22.2 | 16.7 |
| 2-Butanamine, 3-methyl- | 3 | 2 | 1 | 0 | 25.0 | 22.2 | 16.7 |
| Terbutaline, N-trifluoroacetyl-o,o,o-tris(trimethylsilyl)deriv. | 3 | 2 | 1 | 0 | 25.0 | 22.2 | 16.7 |
| Benzeneethanamine, N-[(pentafluorophenyl)methylene]-•beta•,3,4-tris[(trimethylsilyl)oxy]- | 5 | 1 | 2 | 0 | 41.7 | 11.1 | 33.3 |
| 1-Dodecene | 5 | 2 | 2 | 0 | 41.7 | 22.2 | 33.3 |
| 1-Hexanol, 2-ethyl- | 5 | 2 | 2 | 0 | 41.7 | 22.2 | 33.3 |
| Benzaldehyde, 2-methyl- | 6 | 3 | 2 | 0 | 50.0 | 33.3 | 33.3 |
| Cyclohexadecane | 5 | 3 | 2 | 0 | 41.7 | 33.3 | 33.3 |
| 3-Cyclohexen-1-ol, 4-methyl-1-(1-methylethyl)- | 8 | 4 | 2 | 0 | 66.7 | 44.4 | 33.3 |
| Benzoic acid, 2,5-bis(trimethylsiloxy)-, trimethylsilyl ester | 6 | 4 | 2 | 0 | 50.0 | 44.4 | 33.3 |
| 9,10-(1,2-Benzeno)anthracene, 2,3-dimethyl-9,10-dihydro- | 8 | 2 | 3 | 0 | 66.7 | 22.2 | 50.0 |

TABLE 9

List of significant VOCs mostly found in prostate cancer-negative samples. "PC" represents prostate cancer samples; "PCN" represents prostate cancer-negative samples; "Ctrl" represents control samples; "DI" represent deionized water sample.

| | Occurrence | | | | Occurrence Rate (%) | | |
|---|---|---|---|---|---|---|---|
| | PC | PCN | Ctrl | | | | |
| Compounds | (n = 12) | (n = 9) | (n = 6) | DI | PC | PCN | Ctrl |
| Formic acid, 1-(4,7-dihydro-2-methyl-7-oxopyrazolo[1,5-a]pyrimidin-5-yl)-, methyl ester | 0 | 4 | 0 | 0 | 0.0 | 44.4 | 0.0 |
| •alpha•-Methylstyrene | 0 | 3 | 0 | 0 | 0.0 | 33.3 | 0.0 |
| Benzenamine, 4-bromo-3-chloro-N-(4-methylthiobenzylydene)- | 0 | 3 | 0 | 0 | 0.0 | 33.3 | 0.0 |
| E-8-Methyl-9-tetradecen-1-ol acetate | 1 | 4 | 0 | 0 | 8.3 | 44.4 | 0.0 |
| 1,2-Benzenedicarboxylic acid, diisooctyl ester | 1 | 3 | 0 | 0 | 8.3 | 33.3 | 0.0 |
| 1,2-Propanediol, 3-benzyloxy-1,2-diacetyl- | 1 | 3 | 0 | 0 | 8.3 | 33.3 | 0.0 |
| Benzoic acid, 5-methyl-2-trimethylsilyloxy-, trimethylsilyl ester | 1 | 3 | 0 | 0 | 8.3 | 33.3 | 0.0 |
| 13H-Dibenzo[a,i]carbazole | 1 | 4 | 1 | 0 | 8.3 | 44.4 | 16.7 |

The data analysis of the VOCs metabolites occurrence in prostate cancer, prostate cancer-negative, and control samples has indicated difference among those three different types of samples. Though there are VOCs existing exclusively in each category, the occurrence of such VOCs are not 100%. Nonetheless, these VOCs would be considered as the potential indicators of prostate cancer. The prostate cancer specific compounds or compounds groups could be determined by the further study of VOCs. In the next step, peak area ratio of each compound will be analyzed to determine the compounds with significant amount change between different types of samples. Statistic method, including PCA, will be used in assess the acquired compound list. The potential prostate cancer specific compounds or compounds groups may contribute to the metabolomics study of prostate cancer.

Example 3

Volatile Organic Compounds in Urine of Prostate Cancer Patients and Risk Assessment A. Methods Patient recruitment and sample collection. For PCa diagnostic model development, 108 men (aged from 40 to 84) who presented for prostate biopsy for either an elevated PSA or abnormal digital rectal exam were included (Table 10). Of the 108 men, 55 were diagnosed with PCa, while 53 were PCa negative controls. For the development of PCa risk model, additional 34 PCa positive patients were included to attain 89 subjects in PCa risk assessment. Based on the Gleason score (GS) and PSA, these PCa patients were divided into two groups: low-risk group (GS=6, PSA<10) and high-risk group (GS=6 and PSA≥10, or GS>6 with any PSA values) as shown in Table 11. The high risk group was considered to be clinical significant and low risk group as indolent PCa. Urine samples were collected at the medical facilities and stored at −80° C. until chemical analysis.

TABLE 10

Demographic information of prostate cancer and cancer-negative patients in the VOC PCa diagnosis model study. Data are presented as median (interquartile range) for continuous variables and n (%) for categorical variables.

| | Prostate cancer patients | | | Controls | |
|---|---|---|---|---|---|
| | Low risk | High and intermediate risk | P value | Negative Biopsy | p value |
| N | 20 | 35 | | 53 | |
| PSA[a] (ng/mL) | 5.29 (0.08-1987) | | | 2.6 (0.1-18.2) | 0.28[c] |
| | 2.38 (0.1-9.33) | 5.93 (0.08-1987) | 0.28[b] | | |
| Gleason score | | 6-9 | | N/A | |
| 6 | 20 (100) | | | | |
| 7 | | 23 (66) | | | |
| 8 | | 6 (17) | | | |
| 9 | | 6 (17) | | | |

[a]PSA: prostate specific antigen;
[b]The p value from the t-test of the PSA numbers between low grade and high and intermediate grade groups; The p value from the t-test of the PSA numbers between prostate cancer and control groups

TABLE 11

Demographic information of prostate cancer patients in the VOC PCa risk assessment model study. Data are presented as median (interquartile range) for continuous variables and n (%) for categorical variables.

| | Prostate cancer patients | | |
|---|---|---|---|
| | Low risk | High and intermediate risk | p value[a] |
| N | 34 | 55 | |
| PSA (ng/mL) | 5.29 (0.08-1987) | | |
| | 3.95 (0.1-9.33) | 6.21 (0.08-1987) | 0.22 |

TABLE 11-continued

Demographic information of prostate cancer patients in the VOC PCa risk assessment model study. Data are presented as median (interquartile range) for continuous variables and n (%) for categorical variables.

| | Prostate cancer patients | | |
|---|---|---|---|
| | Low risk | High and intermediate risk | p value[a] |
| Gleason score | | 6-9 | |
| 6 | 34 (100) | | |
| 7 | | 38 (69) | |
| 8 | | 11 (20) | |
| 9 | | 6 (11) | |

[a] The p value from the t-test of the PSA numbers between low grade and high risk groups Extraction of VOCs from urine samples. Urine samples were thawed in ice and centrifuged for 10 minutes at 300 g prior to extraction. To extract the VOCs, 1.0 mL of urine supernatant sample, 19.0 mL of DI water, 300 µL of 100 ppm Mirex solution and 600 µL of 2 M hydrochloric acid were added into a 20 mL amber vial. A commercially available Stir Bar coated with polydimethylsiloxane (Twister™, 10 mm×1 mm, Gerstel, Mülheim an der Ruhr, Germany) was then placed into the vial, and the solution was stirred for 2 hours at 1000 rpm. At the end of the stirring, the stir bar was removed from the solution, rinsed with DI water, dried with lint free paper, and placed into a thermal desorption tube for chemical analysis.

Gas Chromatography-Mass Spectrometry analysis. VOCs from urine samples were analyzed in a thermal desorption unit, TDU (Gerstel), coupled with a 6890 GC system and a 5973 N Mass Selective Detector (Agilent Technologies, Wilmington, Del.). The thermal desorption in the TDU was programmed as follows. The initial temperature was set at 45° C. holding for 0.5 min; the temperature was increased to 300° C. at 60° C. min$^{-1}$ and held for 5 min. Desorption gas flow was set at 1.0 mL min$^{-1}$. During desorption, all the desorbed compounds were concentrated in a cold injection system, CIS-4 (Gerstel), at −40° C. prior to GC injection. Once the desorption process was completed, the CIS temperature was ramped to 300° C. at 12° C. sec$^{-1}$ and held for 5 min in a solvent vent mode. The VOCs were separated and analyzed by GC/MS under splitless mode. A ZB-5 ms capillary column (30 m×0.25 mm×0.25 µm, Phenomenex, USA) was used. The oven temperature was programmed as follows: held at 35° C. for 5 min; heated to 300° C. at 10° C. min$^{-1}$, and held for 10 min. The VOCs in urine samples were detected by Mass Selective detector in scan mode (20-500 m/z). The National Institute of Standards and Technology (NIST) Library was used for the identification of VOCs profile in urine sample.

Data processing and statistical analysis. Mirex was used as the internal standard of choice because of its non-existence in urine. The relative intensity of each VOC peak could then be normalized against that of Mirex to enable semi-quantitative analysis of VOCs in the statistical study.

Over 9000 VOCs were detected in the study. To streamline the analysis, VOCs observed in less than 3% of the entire population were removed. The statistical significance of each VOC in both PCa positive vs. PCa negative and high risk PCa vs. low risk PCa was respectively tested by Wilcoxon test, which could accommodate the zero inflation among many VOCs. Heat maps were generated to visualize significant VOCs (p<0.05) among the PCa positive and control groups, and the high and low risk PCa groups.

Applying a liberal cutoff at p=0.2, a larger number of VOCs were selected to develop logistic regression models[47] with either LASSO[51] or SCAD[46] penalty in data fitting for further variable selection. Either 10-fold cross-validation or the generalized cross-validation criterion was used to select the optimal tuning parameter, leading to a final logistic model.

The final logistic model was evaluated via the Receiver Operating Characteristic (ROC) curve and its associated performance was measured on the basis of jackknife prediction[49]. The jackknife cross-validation technique helps avoid over-optimism induced by variable selection. Furthermore, Firth's approach was taken to fit the final logistic model to deal with bias-reduction for small sample size as well as yields consistent estimates even in case of the nearly complete separation in the data[48]. All the analyses are performed using the open-source statistical computing package R[50].

B. Results

The study analyzed VOCs in urine samples collected from 108 patients to develop the "VOCs PCa diagnosis model" and from 89 PCa patients for the "VOCs PCa risk assessment model". VOCs were analyzed by Gas Chromatography/Mass Spectrometry. All VOCs were identified based on their occurrence and relative quantity in the urine.

1. VOCs PCa Diagnosis Model.

A total of 9,144 potential VOCs were detected in urine collected from 108 patients (55 PCa positive and 53 PCa negative age matched controls). Using the Wilcoxon test at statistical significance p<0.05, 254 VOCs were found to be related to PCa positive urine samples and 282 VOCs corresponding to PCa negative ones. The distribution of those selected VOCs in patients was shown in FIG. 6.

A broader range of VOCs were selected into the regression model (cutoff at p=0.20), and 850 potential VOCs were identified. After further selection with $l_1$ regularization, 11 VOCs were selected for the final logistic model (listed in the Table 12). On the basis of predicted probabilities from the final model via jackknife cross-validation, the area under the receiver operating characteristic (ROC) curve (AUC) was 0.92 as shown in FIG. 7A, which indicated a highly promising discrimination power between VOCs in urine of PCa positive and controls. As a comparison, the diagnostic performance of PSA were also tested. The prediction model rendered an AUC of 0.54 and the sensitivity and specificity were 0.44 and 0.74 respectively, indicating a poor discriminating ability of PSA in PCa diagnosis (FIG. 7B). VOC PCa diagnosis model in this study outperformed other biomarkers in PCa diagnosis (Table 13).

2. VOCs PCa Risk Assessment Model.

A total of 89 PCa patients (55 High risk PCa patients and 34 low risk PCa patients) were recruited for the study. Based on the Gleason score (GS) and PSA, these PCa patients were divided into two groups: low-risk group (GS≤6, PSA<10) and high-risk group (GS≤6 and PSA>10, or GS>6 with no restriction on the PSA value) as shown in Table 11. The high risk group was considered to be clinical significant and low risk group reflected indolent PCa.

Figure 8:
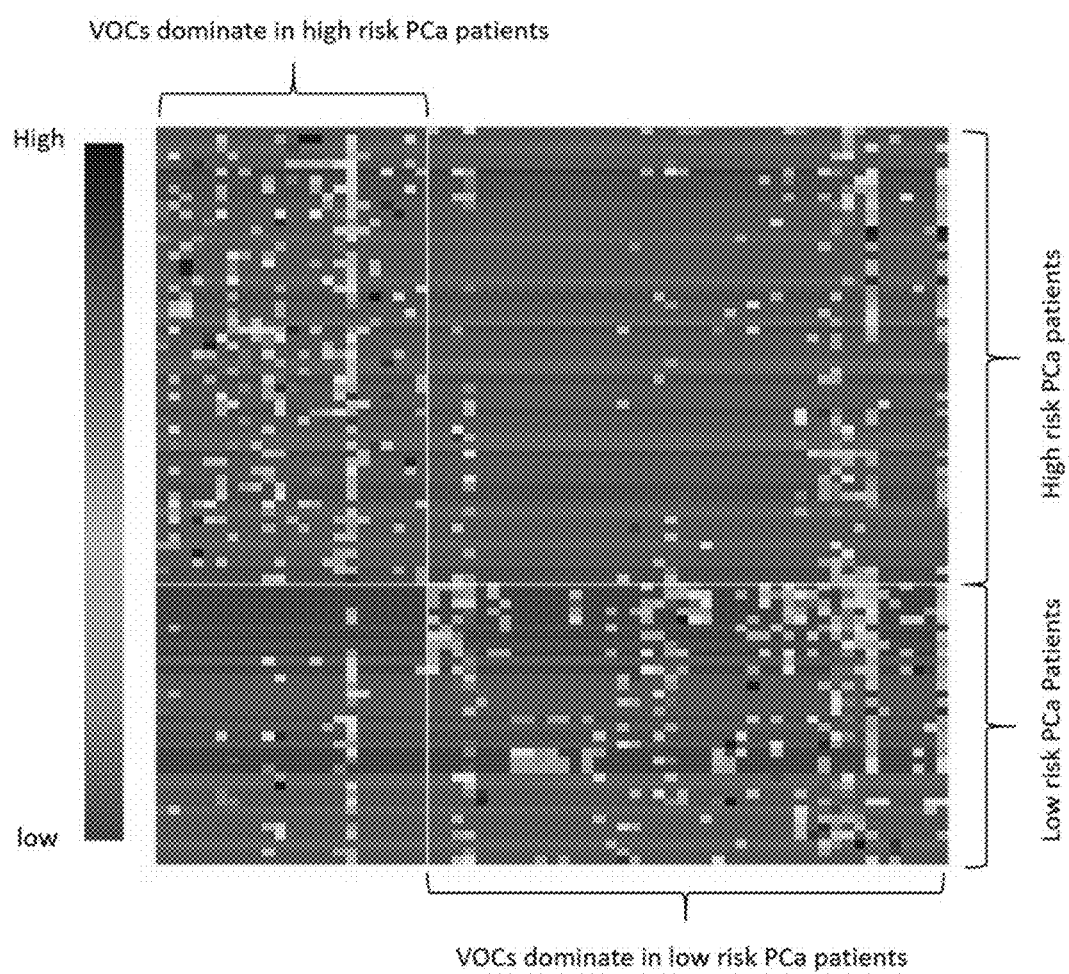
FIG. 8. Illustrates a heat map of significant VOCs by Wilcoxon test (p<0.05) in high risk vs low risk prostate cancer groups of example 3. The correlation between VOCs and patients ranges from low (red) to high (blue).
Figure 9:
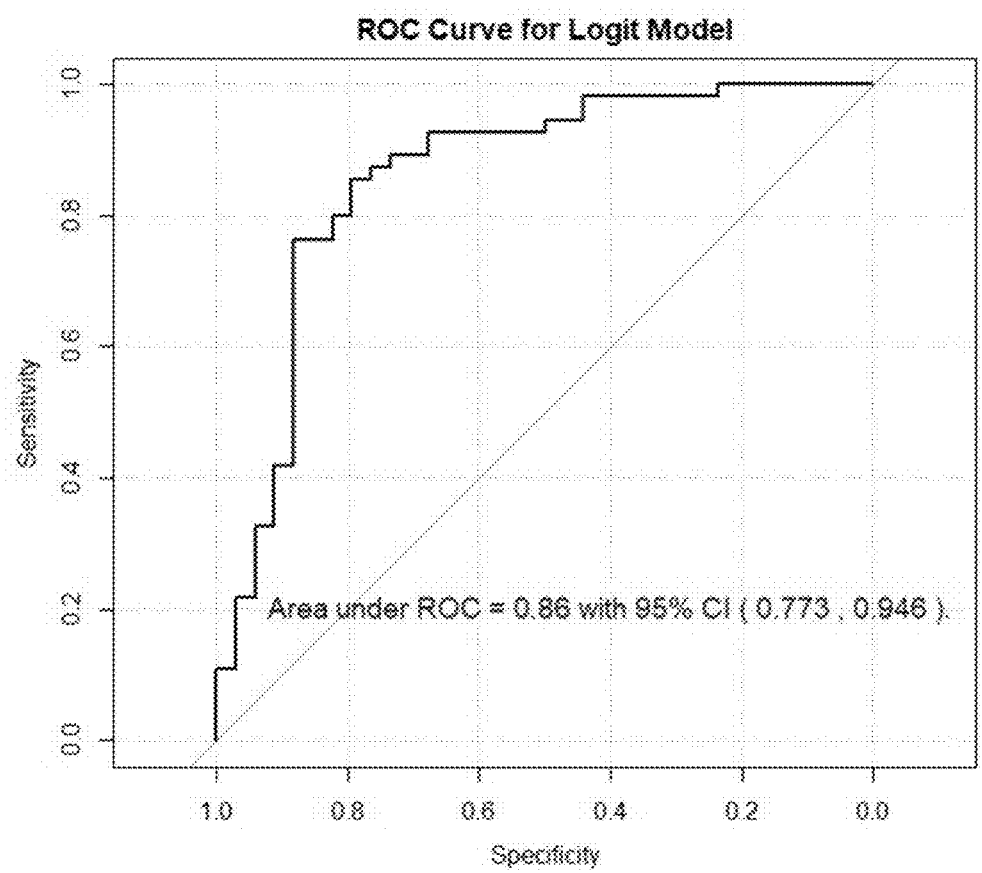
FIG. 9. Illustrates a ROC curve for prostate cancer risk assessment logistic model (Jackknife analysis) with 11 selected VOCs verified in 89 patients.

Using Wilcoxon rank sum test, 23 VOCs were found to be highly related to high-risk PCa and 44 VOCs corresponding to the low risk PCa shown in FIG. 8. After variable screening with a more liberal cutoff at p=0.20, 289 potential VOCs were selected for model development. Using $l_1$ regularization, the final logistic model selected 11 VOCs (listed in the Table 12). On the basis of predicted probabilities from the final model via Jackknife cross-validation, the area under the receiver operating characteristic (ROC) curve is 0.86 as shown FIG. 9, which indicates a highly promising discrimination power of urinary VOCs in PCa high risk assessment.

et al included a similar number of patients as this current work (102 vs. 108 patients). The VOCs were extracted by solid-phase micro-extraction (SPME) fiber. Four VOCs (i.e. 2,6-dimethyl-7-octen-2-ol, pentanal, 3-octanone, and 2-oc-

TABLE 12

VOCs from logistic regression models for prostate cancer diagnosis prediction and risk assessment

| CAS Number | Formula | Chemical Name | Dominating Group | Occurrence | |
|---|---|---|---|---|---|
| | | Selected VOCs for PCa occurrence prediction | | PCa positive | PCa negative |
| 000472-41-3 | C18H20O2 | 4-(3,4-dihydro-2,2,4-trimethyl-2H-1-benzopyran-4-yl)-phenol | PCa negative | 0 | 22 |
| 000995-83-5 | C10H32O4Si5 | 1,1,3,3,5,5,7,7,9,9-decamethyl-pentasiloxane | PCa positive | 35 | 9 |
| 003555-47-3 | C12H36O4Si5 | 1,1,1,5,5,5-hexamethyl-3,3-bis[(trimethylsilyl)oxy]- | PCa positive | 52 | 37 |
| 129086-73-3 | C16H32O3 | Ethyl à-hydroxymyristate trisiloxane | PCa negative | 1 | 19 |
| 075132-80-8 | C3H7Cl5N3P3 | 1-Propylpentachlorotriphosphazene | PCa positive | 47 | 36 |
| 024535-53-3 | C12H8ClNO3S | 4-Nitro-4'-chlorodiphenylsulfoxide | PCa positive | 46 | 23 |
| 1000215-25-2 | C15H22O | 1-(2,4-Dimethylphenyl)-3-(tetrahydrofuryl-2)propane | PCa negative | 0 | 15 |
| 1000126-50-5 | C4H5N3O2 | Imidazole-5-carboxylic acid, 2-amino- | PCa negative | 0 | 15 |
| 101100-38-3 | C15H22O2 | 2,6-di-t-butyl-4-hydroxymethylene-2,3,5,6-detetrahydrocyclohexanone | PCa positive | 23 | 4 |
| 000050-28-2 | C18H24O2 | Estradiol | PCa negative | 4 | 20 |
| 020548-62-3 | C26H42O4 | Phthalic acid, bis(7-methyloctyl) ester | PCa positive | 23 | 8 |
| | | Selected VOCs for PCa risk prediction | | High risk | Low risk |
| 031061-61-7 | C13H20O2 | Tricyclo[4.3.1.1(3,8)]undecane-3-carboxylic acid, methyl ester | Low risk | 2 | 5 |
| 018127-01-0 | C13H18O | 4-(1,1-dimethylethyl)-benzenepropanal | Low risk | 1 | 5 |
| 007206-21-5 | C18H36 | 5-Octadecene, (E)- | High risk | 14 | 15 |
| 020607-72-1 | C6H14N2 | Acetaldehyde, butylhydrazone | Low risk | 19 | 3 |
| 046498-17-3 | C13H13N3 | 3,6-Diamino-9-methylcarbazole | High risk | 0 | 5 |
| 000111-06-8 | C20H40O2 | Hexadecanoic acid, butyl ester | Low risk | 3 | 8 |
| 131316-14-8 | C17H16Os | trans-3'-Methyl-4-(methylthio)chalcone | Low risk | 1 | 9 |
| 092617-73-7 | C13H18O | 2-(1,1-dimethyl-2-propenyl)-3,6-dimethyl-phenol | Low risk | 16 | 3 |
| 054340-85-1 | C12H16 | 1-(2-butenyl)-2,3-dimethyl-benzene | Low risk | 2 | 6 |
| 001153-51-1 | C19H30O | (3alpha,5alpha)-androst-16-en-3-ol | Low risk | 2 | 6 |
| 000621-42-1 | C8H9NO2 | Metacetamol | Low risk | 1 | 5 |

TABLE 13

Sensitivity, specificity, and AUC from various biomarkers in prostate cancer diagnosis

| | Current study | | Potential biomarkers | | | | |
|---|---|---|---|---|---|---|---|
| | VOC | PSA | Iso-PSA (24) | PCA3 (25) | TMPRSS2:ERG (26) | 4Kscore (19) | PHI (22) |
| Sensitivity | 0.89 | 0.44 | 0.90 | 0.684 | 0.243 | | |
| specificity | 0.85 | 0.74 | 0.48 | 0.583 | 0.932 | | |
| AUC | 0.92 | 0.54 | 0.79 | 0.679 | 0.59 | 0.82 | 0.68 |

Mirex was used as the internal standard in the analysis because it does not exist in human, and has a relative longer retention time in GC so that it will not interfere with other VOCs. The introduction of an internal standard to the analysis allowed the semi-quantitative determination of VOCs (i.e. using the ratio of the peak areas between the VOC and the internal standard). As PCa is a heterogeneous disease, the expression of VOCs in continuous data instead of binary representation can add the value of the model development. The continuous data also comprehensively represents the up or down regulation of metabolites in vivo.

For the urinary VOC based PCa diagnostic model, 11 VOCs were selected by the logistic regression. The model was validated among PCa positive and negative urine samples and produced an AUC of 0.92 (FIG. 7a), which indicate a highly promising discrimination power of VOCs in urine for PCa diagnosis. The AUC value is also higher than what was reported by Khalid T, et al in 2015[20]. Khalid tanone) were selected in Khalid's model which was validated to have an AUC at 0.76. As a comparison, the analytical method in this study provided high throughput of VOCs and that could have benefited the selection of broader range of significant VOCs in the model development. That could be a major contribution of a better prediction power in this current VOC PCa diagnosis model than the reported value.

Many other biomarkers were also developed to provide alternatives to address the poor performance of PSA in diagnosis of PCa, including Iso-PSA, prostate cancer antigen 3 (PCA3), 4Kscore, Prostate Health Index (PHI), TMPRSS2:ERG and ConfirmMDx[52-56, 22]. PSA is the prostate specific but not PCa specific, which also contributes to its low accuracy in PCa diagnosis. Among those new markers, IsoPSA, PHI and 4Kscore are all PSA-based assay for PCa risk assessment[52,55,22]. PCA3 is a noncoding RNA that is prostate specific and highly overexpressed in prostate cancer[57]. TMPRSS2-ERG gene fusions are reported to be the predominant molecular subtype of prostate cancer[58]. ConfimMDx is an epigenetic test for PCa diagnosis before prostate biopsy[56]. Again, these methods were not able to provide satisfactory screening for PCa because of either low sensitivity or specificity or both low sensitivity and specificity. On the other hand, metabolomics profiling has been reported to show tremendous promise as one of the "omics" methodologies for PCa diagnosis[35]. Our working rationale was that VOCs in urine reflect the physiological and metabolic status of an individual. As a result, the VOC PCa diagnosis model in this study outperformed those above-mentioned biomarkers in PCa diagnosis Table 13.

Many VOCs selected for PCa screening and risk prediction showed potential correlations to some metabolic mechanisms. For instance, many selected VOCs, such as 5-Octadecene, Hexadecanoic acid, butyl ester, bis(7-methyloctyl) ester, may be involved in the lipogenesis. Androgens and androgen receptor (AR) in prostate have shown to regulate the activity/expression of several enzymes[59] and enhance lipogenesis, which is a metabolic hallmark of many cancer cells that arising from increased activities of fatty acid biosynthetic enzymes (including ACC1, FASN, and stearoyl CoA desaturase (SCD1))[60-62]. These fatty acid related VOCs in urine could be a results of such activities in PCa.

Figure 10:
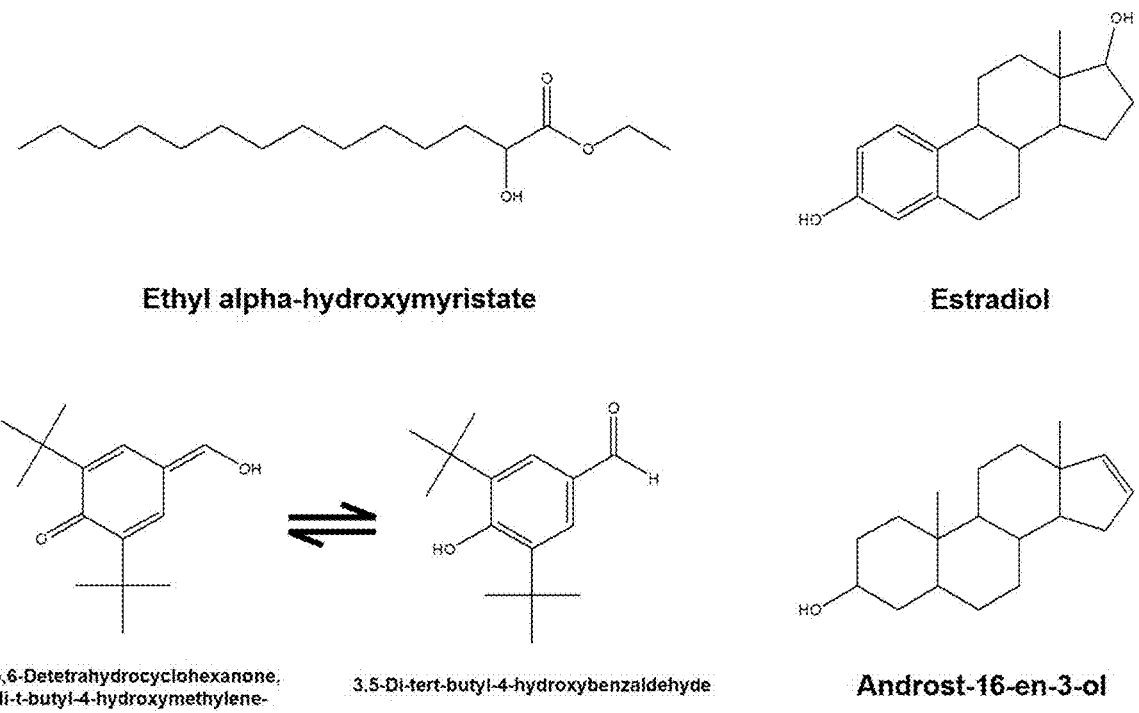
FIG. 10. Illustrates chemical structures of ethyl alpha-hydroxymyristate; estradiol; 2,3,5,6-Detetrahydrocyclohexanone, 2,6-di-t-butyl-4-hydroxymethylene-; 3,5-Di-tert-butyl-4-hydroxybenzaldehyde; and androst-16-en-3-ol.

In the VOC PCa diagnosis model, 5 out of the selected 11 VOCs were up-expressed in PCa negative patients (control group), and 6 were dominated in PCa positive patients as listed in Table 12. Ethyl alpha-hydroxymyristate, as one of the VOCs up-expressed in PCa negative patients, contains the moiety of Alpha-Hydroxymyristic acid or 2-hydroxymyristic acid (shown in FIG. 10). 2-Hydroxymyristic acid is an analog of myristic acid, which can be metabolically activated to form 2-hydroxymyristoyl-CoA in cells. It is a potent inhibitor of myristoyl-CoA:protein N-myristoyltransferase, an enzyme that catalyzes protein N-myristoylation. In another study, 2-hydroxymyristic acid was reported to be able to inhibit the myristoylation and alters the stability of p56$^{lck}$ in T cells. p56$^{lck}$ is a Src family protein-tyrosine kinase that is found predominantly in lymphoid cells[63]. p56$^{lck}$ proteins were reported to be positively expressed in PCa cell lines and tissues[64], and preferentially expressed in metastatic cancer[65]. The up expressed of p56lck proteins may come from the effect of endogenous 2-hydroxymyristic acid. So the relative low level of ethyl alpha-hydroxymyristate in PCa urine samples might indicate the consumption of 2-hydroxymyristic acid in PCa patients.

Another selected VOC dominated in PCa positive group, 2,6-di-t-butyl-4-hydroxymethylene-2,3,5,6-detetrahydrocyclohexanone, is the tautomer of 3,5-di-t-butyl-4-hydroxybenzaldehyde. It was reported to be active in the test of qHTS assay to identify small molecule agonists of the RXR (retinoid X nuclear receptor alpha) signaling pathway: Summary (AID 1159531)[66]. The nuclear expression of RXR alpha receptor subtype is reported to be generally down-regulated in human PCa cell lines and specimens, and the loss or reduction of RXR alpha function is a critical determinant in prostate tumorigenesis[67]. The high level of 2,6-di-t-butyl-4-hydroxymethylene-2,3,5,6-detetrahydrocyclohexanone in PCa positive urine samples may reveal the low utilization of all those types of agonist of RXR signaling pathway due to the loss of RXR alpha function. Estradiol, as an estrogen steroid hormone, is also selected in the predication model of PCa occurrence and is dominated in PCa negative group. The low level of estradiol in PCa positive urine samples of our results is consistent with the perspective study of sex hormone levels of PCa, of which the results revealed that low levels of circulating estradiol may be one of the risk factors of PCa[68].

Among 11 VOCs selected by the regression mode of PCa high risk vs PCa low risk, 9 VOCs were dominated in PCa low risk patients and 2 were dominated in PCa high risk groups as listed in Table 12. Androstenol, dominating in PCa low risk group, has a structure similar to that of androgens. Androstenol could be efficiently transformed from the precursor 5,16-androstadien-3β-ol (a sex steroid) through enzymatic activities including 3β-hydroxysteroid de-hydrogenase, 5α-reductase and 3α-hydroxysteroid dehydrogenase[69]. Of those three enzymes, 3β-hydroxysteroid de-hydrogenase and 5α-reductase were reported to be involved in PCa development and progression[70,71]. And studies also showed that androstenol could modulate the activity of CAR (constitutive androstane receptor) and PXR (pregnane X receptor, also known as steroid and xenobiotic receptor SXR) and the expression of some cytochrome P450 drug-metabolizing enzymes[72,73]. A combined analysis with CYP3A4 expression revealed that the low expression of the SXR and CYP3A4 was a significantly unfavorable prognostic factor for PCa in a multivariate analysis. It was suggested that the downregulation of the SXR, and consequently, its target CYP3A4 gene might play a significant role in PCa progression. Androstenol might exert tumor-inhibitory effects on PCa by increasing SXR expression and enhancing androgen clearance[74]. Therefore, the lower level of androstenol in the high risk group was consistent with the reported biological effect, i.e. relating the down regulation of SXR activities with the progression of PCa.

Using VOCs in urine is a non-invasive and promising method for both PCa diagnosis and risk assessment. The biological and chemical significance of some selected VOCs in this study could link to specific metabolic pathways in PCa progression and could be further studied to provide supporting evidence for the upstream proteomic pathways. Even with a considerably small sample size, the VOC models showed very promising discriminating power between PCa and negative control, as well as between high risk and low risk PCa. Results showed that urinary VOCs could likely be translated into a clinically viable, highly sensitive, cost-effective portable diagnostic assay for PCa and may help identify patients with clinically significant PCa.

Example 4

Volatile Organic Compounds in Urine of Renal Cell Carcinoma Patients

A. Methods

Study design. For RCC diagnostic model development, 111 urine samples in total were obtained from a) 77 patients preoperatively on the day of surgery who were undergoing partial or radical nephrectomy with a presumptive diagnosis of RCC based on a CT imaged renal mass (and whose postoperative pathology diagnosis established clear cell, papillary, or chromophobe RCC); b) 24 patients RCC negative based the imaged renal mass; and c) 10 defined healthy controls.

Figure 11:
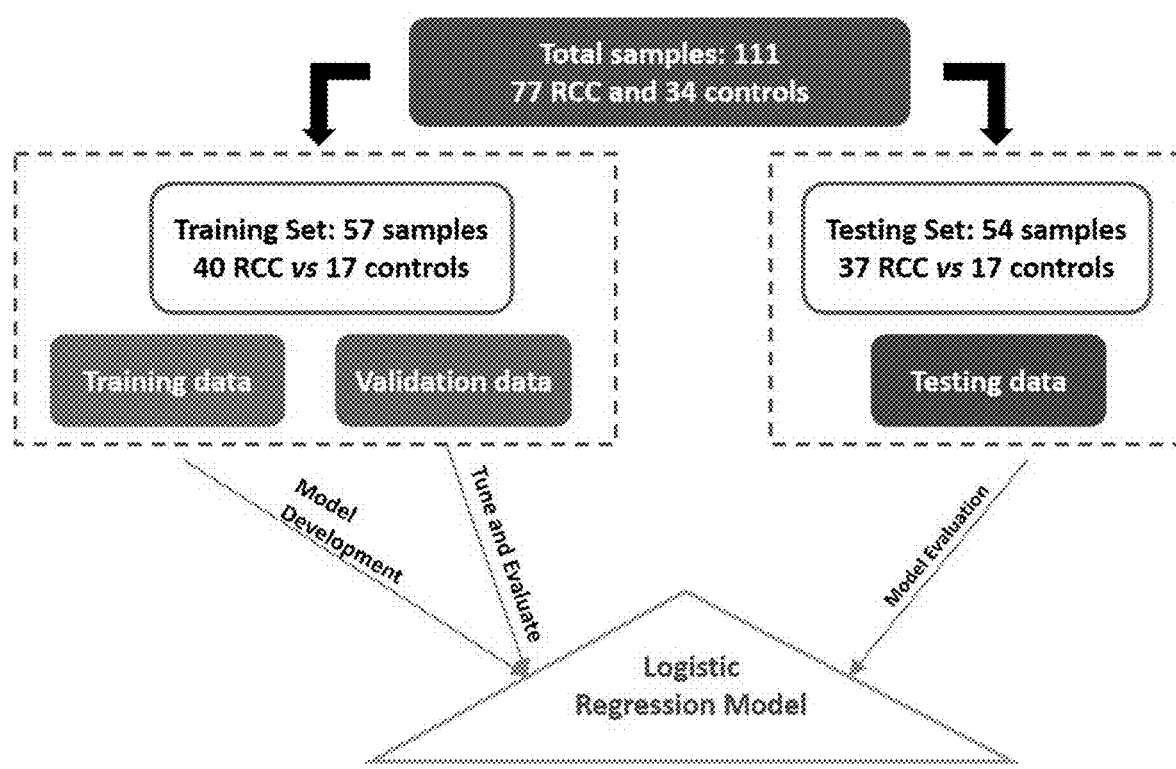
FIG. 11. Illustrates study design of VOCs in urine of renal cell carcinoma patients, as disclosed in example 4.

In the training set of RCC diagnose model, 40 out of 77 pathologically diagnosed RCC patients were designated as cancer group and 17 of 24 RCC negative patients were control group. To evaluate the final performance of the RCC diagnostic model, the rest 37 RCC patients and 7 RCC negative and 10 healthy controls were assigned as the cancer group and control group in testing set of RCC diagnose model shown in FIG. 11, Table 14.

Urine samples were collected at the medical facilities and stored at −80° C. until chemical analysis.

TABLE 15

Demographic information of the example 4

|  | Training Set | | Testing Set | |
| --- | --- | --- | --- | --- |
|  | Cancer Group | Control Group | Cancer Group | Control Group |
| Number | 40 | 17 | 37 | 17 |
| Male | 39 | 13 |  |  |
| Female | 18 | 4 |  |  |
| Cancer type |  |  |  |  |
| clear cell RCC | 34 |  | 35 |  |
| papillary RCC | 4 |  | 2 |  |
| chromophobe RCC | 2 |  | 0 |  |
| Tumor grade |  |  |  |  |
| 1 | 1 |  | 2 |  |
| 2 | 15 |  | 18 |  |
| 3 | 13 |  | 10 |  |
| 4 | 8 |  | 7 |  |
|  | 3 |  |  |  |

Chemicals and Materials. All chemicals used were of analytical grade. Mirex (99.0%, Dr. Ehrenstorfer GmbH, Germany), the internal standard, was purchased from the National Institute of Standards and Technology (NIST). Mirex solution at 100 ppm was prepared in methanol. Methanol was purchased from Burdick & Jackson (Muskegon, Mich., USA). Hydrochloric acid (HCl, 37%) were purchased from Sigma-Aldrich (St. Louis, Mo., USA). Ultra-pure deionized water from Milli-Q system (Millipore, Bedford, Mass., USA) was used in the preparation of HCl solution and dilution of urine samples.

Extraction of VOCs from urine samples. Urine samples were thawed in ice and centrifuged for 10 mins at 300 g. In a 20 mL amber vial, 1.0 mL of urine supernatant sample, 19 mL of DI water, 300 μL of 100 ppm Mirex solution and 600 μL of 2 M hydrochloric acid were added. A commercially available Stir Bar (Twister™, 10 mm×1 mm, Gerstel, Mülheim an der Ruhr, Germany) was then placed into the vial, and the solution was stirred for 2 hours at 1000 rpm. The stir bar was then removed from the solution, rinsed with DI water, dried with lint free paper, and placed into a thermal desorption tube for chemical analysis.

Gas Chromatography-Mass Spectrometry analysis. VOCs from urine samples were analyzed in a thermal desorption unit, TDU (Gerstel), coupled with a 6890 GC system and a 5973 N Mass Selective Detector (Agilent Technologies, Wilmington, Del.). VOCs from urine samples were analyzed in a thermal desorption unit, TDU (Gerstel), coupled with a GC/MS system. The initial TDU temperature was 45° C. After holding for 0.5 min, the temperature was increased to 300° C. at 60° C. min−1 and held for 5 min. Desorption gas flow was set at 1.0 mL min−1. During desorption, all the desorbed compounds were concentrated in a cold injection system, CIS-4 (Gerstel), at −40° C. prior to GC injection. Once the desorption process was completed, the CIS temperature was ramped to 300° C. at 12° C. sec−1 and held for 5 min in a solvent vent mode. Splitless mode was employed for the GC analysis. A ZB-5 ms capillary column (30 m×0.25 mm×0.25 μm, Phenomenex, USA) was used. The oven temperature was programmed as follows: held at 35° C. for 5 min; heated to 300° C. at 10° C. min−1, and held for 10 min. The VOCs in urine samples were detected by Mass Selective detector in scan mode (20-500 m/z). The National Institute of Standards and Technology (NIST) Library was used for the identification of VOCs profile in urine sample Data processing and statistical analysis. Mirex was used as the internal standard of choice because of its non-existence in urine. The relative intensity of each VOC peak could then be normalized against that of Mirex to enable semi-quantitative analysis of VOCs in the statistical analysis. PSA of patients and their VOCs profiles were used in statistical analysis. The statistical significance of each VOC was tested by Wilcoxon test. Heat maps were generated to visualize significant VOCs ($p<0.05$) among the PCa positive and control groups. Applying a liberal cutoff at $p=0.2$, a larger size of VOCs was applied to develop a logistic regression model was applied for further selection of noteworthy VOCs. The model based on these significant VOCs in PCa screening was then evaluated by cross-validation.

The VOC-based diagnostic tool was developed via logistic regression.[47] VOCs with less than 3 observations were removed. Then variable screening of VOCs was performed based on the nonparametric Wilcoxon rank-sum test to accommodate the zero inflation among many VOCs. A liberal cutoff threshold $p=0.2$ was applied to select a larger number of significant VOCs for regularized logistic regression with either LASSO[51] or SCAD[46] penalty to fit the data for further variable selection. Either 10-fold cross-validation or the generalized cross-validation criterion was used to select the optimal tuning parameter, leading to a final logistic model. The final logistic model was evaluated via the Receiver Operating Characteristic (ROC) curve and its associated performance was measured on the basis of its jackknife prediction (Kleinbaum and Klein, 2010).[49] The jackknife cross-validation technique helps avoid over-optimism induced by variable selection. Furthermore, to deal with the nearly complete separation in the data, Firth's (1993) approach[48] was taken to fit the final logistic model. All the analyses are performed using the open-source statistical computing package R[50].

B. Results

All VOCs were identified based on their occurrence and relative quantity in the urine. The relative quantity of each VOC was determined through being normalized by the spiked Mirex (the internal standard, IS), of which no inference was found to the VOCs in vivo.

Figure 12:
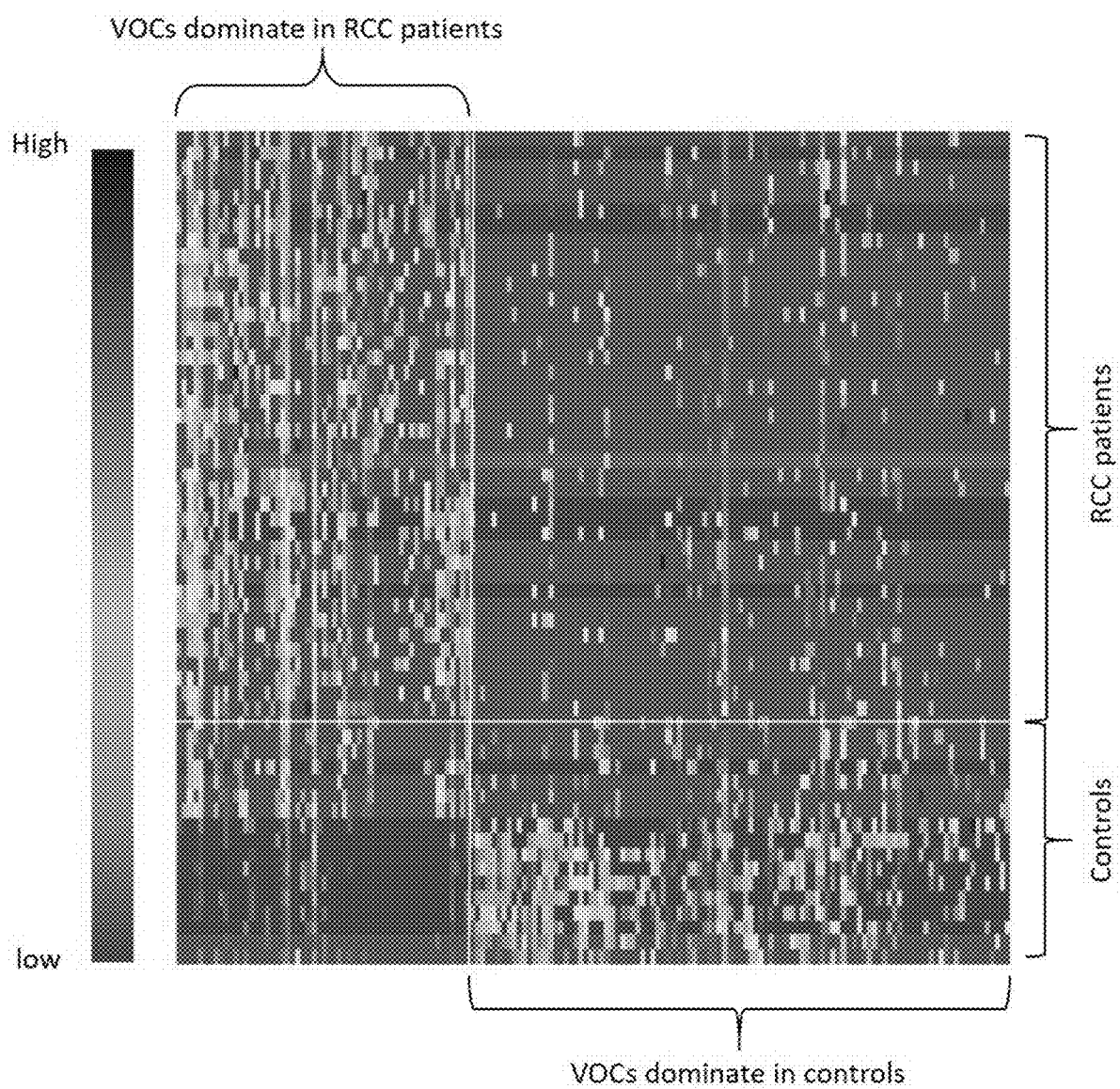
FIG. 12. Illustrates heat map of selected VOCs (p<0.05) in Wilcoxon test of RCC samples vs controls, as disclosed in example 4. The correlation between VOCs and patients ranges from low (red) to high (blue).

A total of 6,075 potential VOCs were detected in urine collected from 57 patients (40 cancer patients and 17 age matched controls). Using the Wilcoxon rank sum test at statistical significance $p=0.05$, 58 VOCs were found to be related to cancer group urine samples and 104 VOCs corresponding to controls. The distribution of those selected VOCs in patients was shown in FIG. 12.

Figure 13A:
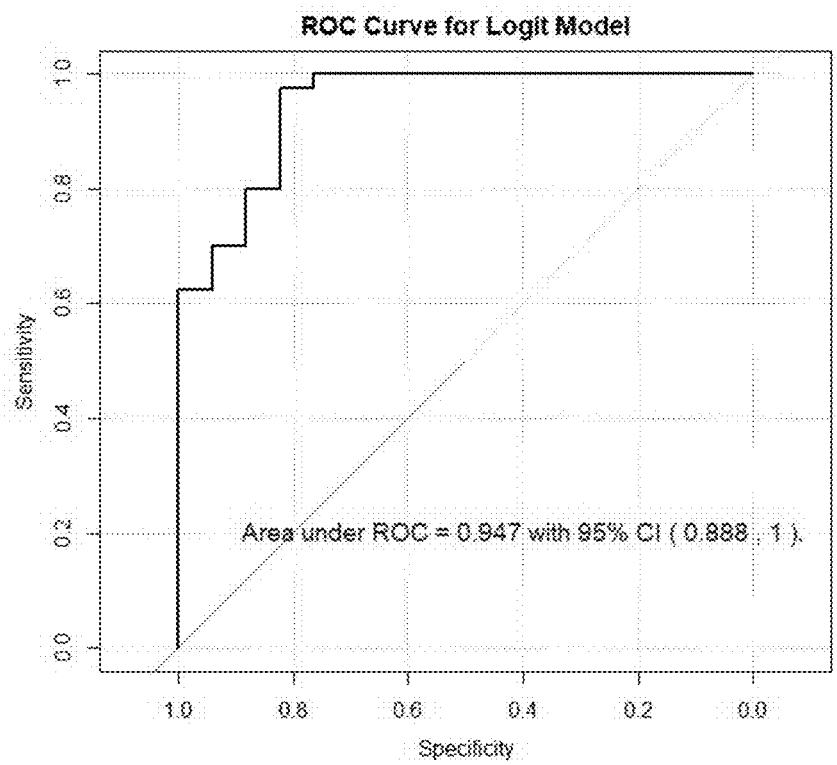
FIGS. 13A-B. Illustrates (A) ROC curve for RCC diagnosis logistic regression model (Jackknife analysis) with 10 selected VOCs in the same 111 patients of example 4; (B) The ROC curve for logistic model in testing group of example 4.

A broader range of VOCs were selected into the regression model (cutoff at $p=0.20$), and 366 potential VOCs were identified. After further selection with $l_1$ regularization, the final logistic model selected 10 VOCs (listed in the Table 16). The difference of all those 10 VOCs were significant (Wilcoxon rank sum test, $P<0.0252$) between cancer group and control group. And 6 of those 10 VOCs were dominated in control group and 4 dominated in cancer group. Then, the performance of this RCC diagnostic model was validated in those 57 patients. On the basis of predicted probabilities from the final model via jackknife cross-validation, the area under the receiver operating characteristic (ROC) curve (AUC) was 0.95 with confidence interval 0.89 to 1 as shown in FIG. 13A, which indicated a highly promising discrimination power between VOCs in urine of RCC patients and controls. The sensitivity and specificity of this RCC diagnostic model (normalized to Mirex) to identify patients with RCC was determined using ROC analysis. Compared to controls, this diagnostic model had 95% sensitivity and 82% specificity, with an area under the ROC (AUC) of 0.95 (Table 17).

Figure 13B:
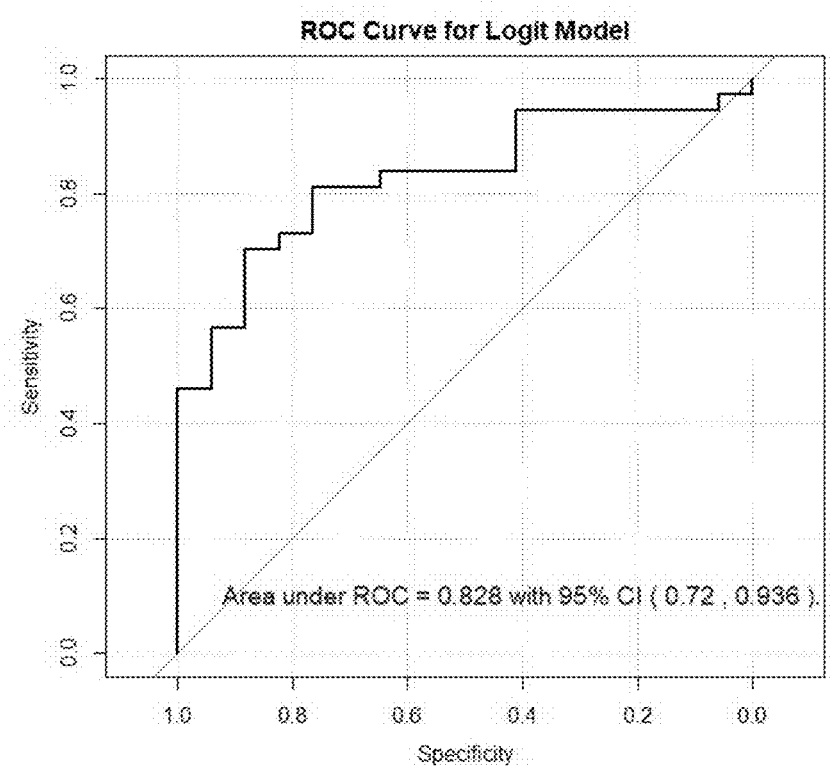

To evaluate the performance of the above RCC diagnostic model, the urine profile of another cohort of patients were analyzed. Via Jackknife cross-validation, the area under the ROC curve is 0.83 with confidence interval 0.72 to 0.94 as shown FIG. 13B. The sensitivity and specificity of this RCC diagnostic model (normalized to Mirex) to identify patients with RCC in new testing data set was determined using ROC analysis. Compared to controls, this diagnostic model had 81% sensitivity and 76% specificity, with an area under the ROC (AUC) of 0.83 (Table 17), which verified the promising discrimination power of urinary VOCs in PCa high risk assessment.

sample sizes which will be an important factor for clinical translatability. Unlike gas-sensor (such as E-nose)[21], the GC/MS can provide much detailed information on the compound identity for future metabolomics and physiological studies. In this study, the VOCs detected in each sample were confirmed through the NIST library report. All samples were analyzed in a blinded and coded fashion in instrument analysis.

An internal standard was introduced so that semi-quantitative levels (i.e. relative peak area ratio to internal standard) for each VOC in statistical analysis can be performed. All the VOCs profiles were normalized to Mirex, the internal standard in the analysis because of the non-existence in human and a relative longer retention time in GC. Unlike the determination protein biomarkers, urine aquaporin-1 (AQP1) and perilipin-2(PLIN2), of RCC reported by Jeremiah J. Morrissey et al[75], the concentration of VOCs in this study was not normalized to the concentration of urine creatinine, which is suggested to be used to minimize the

TABLE 16

VOCs selected in logistic regression model for RCC diagnose

| CAS | Formula | Chemical Name | Dominating Group | p value | Occurrence RCC | controls |
|---|---|---|---|---|---|---|
| 000292-64-8 | C8H16 | Cyclooctane | controls | 0.0001 | 1 | 7 |
| 001120-21-4 | C11H24 | Undecane | controls | 0.0004 | 21 | 15 |
| 001020-31-1 | C14H22O2 | 1,2-Benzenediol, 3,5-bis(1,1-dimethylethyl)- | controls | 0.0006 | 4 | 9 |
| 003557-49-1 | C21H15N | 7H-Dibenzo[b,g]carbazole, 7-methyl- | controls | 0.0034 | 11 | 12 |
| 1000126-50-5 | C4H5N3O2 | Imidazole-5-carboxylic acid, 2-amino- | RCC | 0.0043 | 19 | 1 |
| 1000272-50-0 | C13H17N3O4 | Acetamide, 2-(2,4-dimethoxybenzylidenehydrazino)-N-ethyl-2-oxo- | controls | 0.0116 | 1 | 4 |
| 1000191-72-0 | C20H40O3Si2 | 4-Octynoic acid, 7-(t-butyldimethylsilyloxy)-, t-butyldimethylsilylester | controls | 0.0128 | 1 | 4 |
| 000822-67-3 | C6H10O | 2-Cyclohexen-1-ol | RCC | 0.0185 | 11 | 0 |
| 000124-19-6 | C9H18O | Nonanal | RCC | 0.0198 | 40 | 16 |
| 024535-53-3 | C12H8ClNO3S | 4-Nitro-4'-chlorodiphenylsulfoxide | RCC | 0.0252 | 21 | 5 |

TABLE 17

Sensitivity, specificity, and AUC in training set and testing set

|  | Sensitivity | Specificity | Accuracy | AUC |
|---|---|---|---|---|
| Training | 95.00% | 82.35% | 91.23% | 0.95 |
| Testing | 81.08% | 76.47% | 79.63% | 0.83 |

A urinary VOC based RCC diagnostic model that included 10 VOCs was developed using logistic regression. VOCs based RCC diagnostic model had favorable sensitivity and specificity. In RCC patients compared with RCC negative patients and normal healthy individuals, for two separate comparison group, sensitivity was 95% and 81%, the specificity was 82% and 76%, and the area under ROC was 0.95 and 0.83 for training data set and testing data set, respectively. Therefore the overall high degree of sensitivity and specificity establishes the clinical validity of this VOCs based RCC diagnostic model for the first time.

The analytical method developed in this study allowed an fast and efficient analysis of VOCs without tedious sample preparation. The solventless sample preparation technique, Stir Bar Sorptive Extraction, can preserve the sample integrity and permit effective analyses for processing large impact of hydration status from patient to patient or in the same patient over time[76], because 1) there is a significant lag between the time of injury in kidney and the time that the concentration of creatinine achieve the threshold required to diagnosis kidney disease, which reveal the possible inconsistent concentration of creatinine; 2) there is no significant differences observed between creatinine normalized and non-normalized results in this protein biomarkers paper; and 3) this investigation is designed to test the performance of novel VOCs based model in RCC diagnosis without normalizing to any biomarker of renal disease.

Five phases of screening biomarker development were proposed Margaret Sullivan Pepe et al 2001.[76] However, this study didn't progress consecutively through those five phase. In this investigation, the training and testing set design began with phase 2, clinical assay and validation, and phase 3, retrospective longitudinal. The phase 1, preclinical exploratory, are being investigated along with the phase 2 and phase 3 in this study.

The potential of urinary VOCs used in RCC diagnose has been highlighted in previous studies.[77-79] One major difference between current study and those studies was predication purpose of the experimental design. The purpose of most previous studies were focused on the searching of specific VOCs in RCC patients without further validation.[77,78] In the study reported by Marica Monteiro in 2017[79], the selected VOCs was validated in different patients group besides the searching of specific VOCs, but the performance of VOCs in differentiating RCC patients and controls was not determined. The prediction value of VOCs based diagnostic model were determined through the design of testing set in this studies with AUC, sensitivity, specificity, and accuracy calculation. Another major difference is the introduction of internal standard, Mirex, which enables the relative more accurate quantity determination of VOCs in urine. Two urinary exosomal proteins, AQP-1 and PLIN2 have shown promise as the biomarkers in RCC diagnosis.[75] However, as the VOCs based screening model developed and validated in this study, it has great potential to be developed as a more universal screening tool of almost all types of RCC because of the metabolic distinction shown with each selected VOC between cancer patients and controls, whereas AQP-1 and PLIN2 can be found in clear cell and papillary RCC but not in the chromophobe subtype of RCC. Unlike the ELISA detection methods of AQP-1 and PLIN2, the VOCs based diagnostic model could be developed as a high throughput and fast screening method in clinic enabled by high performance GC/MS and statistic assistance. Last but not least, there is a great potential to improve the VOCs based diagnostic model, like implementing a larger scale of investigation with all types of RCC.

VOCs in urine reflect the physiological and metabolic status of an individual. Dysregulated metabolism is a cancer hallmark and presents opportunities for cancer diagnostics, prognostics, and therapeutics.[80]

VOCs selected for RCC screening model were studied. When examining their chemical structures, Undecane, Cyclooctane, and Nonanal may be involved in peroxidation of fatty acids. Nonanal, as one of the VOCs dominated in RCC patients, was also identified as a volatile biomarkers in lung cancer and liver cancer studies.[81,82] Nonanal ($C_9H_8O$) could be the peroxidation products of oleic acid ($C_{18}H_{34}O_2$), which is one of the main (poly) unsaturated fatty acids (P)UFA in vivo and has potent anti-inflammatory properties.[83,84] 3,5-bis(1,1-dimethylethyl)-1,2-Benzenediol (or 3,5-DI-Tert-butylcatechol), as a phenolic antioxidant, is dominated in control patients. 3,5-DI-Tert-butylcatechol has been reported in the utility of transcriptional activation of the glutathione S-transferase Ya subunit and quinone reductasegenes through antioxidant responsive element (ARE) sequence, which responsive to reactive oxygen species and thus may represent part of a signal transduction pathway that allow eukaryotic cells to sense and respond to oxidative stress.[85]

Prospective use of VOCs based RCC diagnostic model to screen and identify RCC presages a potential clinical use of VOCs model. The populations of RCC patients, RCC negative patients and healthy controls were all representative of populations which might be screened for RCC using these biomarkers. Thus a major implication of this investigation is that wider application of VOCs based diagnostic model might be suitable for population screening for RCC. Even with a considerably small sample size, the VOCs based model showed very promising discriminating power between RCC and control patients.

This method supports the ability of urinary VOCs based diagnostic model to early and non-invasive screening RCC patients. Overall, it validates the clinical utility of urinary VOCs based diagnostic model as the biomarker for RCC.

REFERENCES

1. World Health Organization. CANCER CONTROL: A GLOBAL SNAPSHOT IN 2015. World Health Organization; 2016.
2. American Cancer Society. Cancer Facts & Figures 2016. Atlanta, Ga.: American Cancer Society; 2016.
3. American Cancer Society. Tests for Prostate Cancer. www.cancer.org/cancer/prostate-cancer/detection-diagnosis-staging/how-diagnosed.html#references accessed on Mar. 11, 2016.
4. Catalona et al., *JAMA* 277:1452-55 (1997).
5. Labrie et al. *J Urol* 147:846-51 (1992).
6. Carlson et al., *Urology* 52:455-61 (1998).
7. Ashley et al., *Analytical chemistry* 64:1021-29 (1992).
8. Phillips et al., *Journal of Chromatography B: Biomedical Sciences and Applications* 729:75-88 (1999).
9. Gallagher et al., *British Journal of Dermatology* 159:780-91 (2008).
10. de Lacy Costello et al., Volatile organic compounds (VOCs) found in urine and stool. (Elsevier, Amsterdam, The Netherlands, 2013).
11. Amann and Smith, Volatile VOCs: non-invasive diagnosis in physiology and medicine. (Newnes, 2013).
12. Balseiro and Correia, *Medical hypotheses* 66:270-72 (2006).
13. Cornu et al., *European urology* 59:197-201 (2011).
14. Willis et al., *Cancer VOCs* 8:145-53 (2011).
15. Boedeker et al., *Interactive cardiovascular and thoracic surgery* 14:511-15 (2012).
16. Bjartell, *European urology* 59:202-03 (2011).
17. Taverna et al., *The Journal of urology* 193:1382-87 (2015).
18. Peng et al., *Nature nanotechnology* 4:669-73 (2009).
19. Filipiak et al., *Cancer Epidemiology and Prevention VOCs* 19:182-95 (2010).
20. Khalid et al., *PloS one* 10:e0143283 (2015).
21. Nakhleh et al., Diagnosis and Classification of 17 Diseases from 1404 Subjects via Pattern Analysis of Exhaled Molecules. ACS nano (2016).
22. Klein et al., *European Urology* (2017).
23. Aggio et al. *Journal of breath research* 10:017106 (2016).
24. Wild and Seber, (Chapter, 2011).
25. Pohar et al., *Metodoloski zvezki* 1:143 (2004).
26. Kohavi, *Ijcai*. 1137-45 (Stanford, Calif.).
27. Evans et al., *Journal of medicinal chemistry* 31:2235-46 (1988).
28. Nicolaou et al. *Journal of the American Chemical Society* 122:9939-53 (2000).
29. Handratta et al., *Journal of medicinal chemistry* 48:2972-84 (2005).
30. Njar and Brodie, (ACS Publications, 2015).
31. DeVore and Scott, *Nature* 482:116-19 (2012).
32. Chu et al., *Cell death and disease* 6:e1686 (2015).
33. Thoma, *Nature Reviews Urology* (2016).
34. Huxtable, *Physiol rev* 72:101-63 (1992).
35. Trock, in Urologic Oncology: Seminars and Original Investigations. 572-581 (Elsevier).
36. Hahn et al., *Cancer research* 57:3398-3401 (1997).
37. Thysell et al., *PLoS One* 5:e14175 (2010).
38. MacKinnon et al., *Metabolomics* 8:1026-36 (2012).
39. Sreekumar et al., *Nature* 457:910-14 (2009).
40. Nemer and Elwyn, *Journal of Biological Chemistry* 235:2070-74 (1960).
41. Wilson et al., *Journal of Biological Chemistry* 235:3539-43 (1960).

42. Greenberg, Chemical pathways of metabolism. (Academic Press, 2014).
43. Locasale, *Nature reviews Cancer* 13, 572-83 (2013).
44. Yang and Vousden, *Nature Reviews Cancer* (2016).
45. Harwood, *Annual Review of Plant Physiology and Plant Molecular Biology* 39:101-38 (1988).
46. Fan and Li, (2001), *Journal of the American Statistical Association*, 96:1348-60.
47. Fan and Lv, (2008), *Journal of the Royal Statistical Society, Series B*, 70(5):849-911.
48. Firth, (1993), *Biometrika*, 80(1):27-38.
49. Kleinbaum and Klein, (2010). Logistic Regression, A Self-Learning Text. 3rd Edition. Springer-Verlag: New York, N.Y.
50. R Core Team (2017). R: A language and environment for statistical computing. R Foundation for Statistical Computing, Vienna, Austria. URL https://www.R-project.org/.
51. Tibshirani, (1996), *Journal of the Royal Statistical Society, Series B*, 58:267-88.
52. Parekh et al., *European urology*, 68: 464-70 (2015).
53. Leyten et al., *European urology*, 65: 534-42 (2014).
54. Chun et al., *European urology*, 56: 659-68 (2009).
55. Loeb and Catalona, *Therapeutic advances in urology*, 6: 74-7 (2014).
56. Wojno et al., *American health & drug benefits*, 7: 129 (2014).
57. Hessels et al., *Clinical Cancer Research*, 13: 5103-8 (2007).
58. Tomlins et al., *Neoplasia*,10: 1771N1-88IN9 (2008).
59. Corbin and Ruiz-Echevarría, *International journal of molecular sciences*,17: 1208 (2016).
60. Menendez and Lupu R, *Nature Reviews Cancer*, 7: 763-77 (2007).
61. Swinnen et al., *Current Opinion in Clinical Nutrition & Metabolic Care*, 9: 358-65 (2006).
62. Igal, *Carcinogenesis*, 31:1509-15 (2010).
63. Nadler et al., *Biochemistry*, 32: 9250-5 (1993).
64. Noguchi et al., *The Prostate*, 57: 80-92 (2003).
65. Harada et al., *International journal of clinical oncology*, 8: 193-9 (2003).
66. National Center for Biotechnology Information. PubChem Compound Database; CID=73219 hpnnngc.
67. Zhong et al., *Cancer biology & therapy*, 2:179-84 (2003).
68. Gann et al., *Journal of the National Cancer Institute*, 88:1118-26 (1996).
69. Dufort et al., *The Journal of steroid biochemistry and molecular biology*, 77:223-7 (2001).
70. Devgan et al., *The Prostate*, 33: 9-12 (1997).
71. Thomas et al., *The Prostate*, 63: 231-9 (2005).
72. Forman et al., Nature, 395: 612 (1998).
73. Moore et al., *Journal of Biological Chemistry*, 275: 15122-7 (2000).
74. Fujimura et al., *Cancer science*, 103:176-80 (2012).
75. Morrissey et al., *JAMA oncology*, 1: 204-212 (2015).
76. McMahon and Waikar S S, *American Journal of Kidney Diseases*, 62: 165-178, (2013).
77. Monteiro et al., *European Journal of Cancer*, 50:1993-2002 (2014).
78. Wang et al., *Biomedical reports*, 5:68-72 (2016).
79. Monteiro et al., *Journal of cellular and molecular medicine*, 21: 2092-2105 (2017).
80. Hakimi et al., *Cancer cell*, 29: 104-116 (2016).
81. Xue et al., *Rapid Communications in Mass Spectrometry: An International Journal Devoted to the Rapid Dissemination of Up-to-the-Minute Research in Mass Spectrometry*, 22: 1181-1186 (2008).
82. Fuchs et al., *International Journal of Cancer*, 126: 2663-2670 (2010).
83. Andreoli et al., *Rapid Communications in Mass Spectrometry* 17: 637-645 (2003).
84. Liu et al., *American Journal of Physiology-Renal Physiology*, 295: F942-F949 (2008).
85. Rushmore et al., *Journal of Biological Chemistry* 266: 11632-11639 (1991).
86. Siegel et al., *Cancer statistics*, 2018. *CA: a cancer journal for clinicians*, 68:7-30 (2018).
87. Eble et al., *World Health Organization Classi*, (2004).
88. Ather et al., *Urology Journal*, 7:1-9 (2010).
89. Moch et al., *European urology*, 70: 93-105 (2016).
90. Rodrigues et al., *Translational research*, 180: 1-11 (2017).
91. Lam et al., *World journal of urology*, 23: 202-212 (2005).
92. Cooperberg, *Cancer*, 113: 3062-6 (2008).
93. Wilt et al., *Annals of internal medicine*, 148: 435-48 (2008).
94. Thompson et al., Journal of the National Cancer Institute, 98: 529-34 (2006).
95. Cooperberg et al., The Journal of urology, 173: 1938-42 (2005).
96. Weiss and Kim, *Nature Reviews Nephrology*, 8: 22 (2012).

The invention claimed is:
1. A method for treating prostate cancer, comprising:
(i) determining that a patient has a prostate cancer comprising the steps of:
 (a) obtaining an urine sample from the subject and subjecting the sample to sorptive extraction forming a processed sample;
 (b) determining a level of at least one volatile organic compound associated with prostate cancer selected from the group consisting of 2-undecanone, N-(2-hydroxyethyl)-decanamide, 2-benzyl sulfonyl-benzimidazole, methyl 1-octadecenyl ether, bicyclo[4.2.0]octa-1,3,5-triene, 1-chloro-nonadecane, 3-methylene-4-phenyl-tricyclo[5.2.1.0(2,6)]decane, 1-decen-3-yne, 2-phenyl-2,2'-bi-1,3-dioxolane, 2-ethylacridine, N-[4-(trimethylsilyl)phenyl]-acetamide, 2-methoxy-2-methylbut-3-ene, N-methyltaurine, 1-bromo-tetracosane, methoxyacetic acid, heptadecyl ester, 4-(3,4-dihydro-2,2,4-trimethyl-2H-1-benzopyran-4-yl)-phenol, 2-amino-1,1,3,3,5,5,7,7,9,9-decamethyl-pentasiloxane, 1,1,1,5,5,5-hexamethyl-3,3-bis[(trimethylsilyl)oxy], ethyl alpha-hydroxymyristate, 1-Propylpentachlorotriphosphazene, 4-Nitro-4'-chlorodiphenylsulfoxide, (2,4-Dimethylphenyl)-3-(tetrahydrofuryl-2)propane, imidazole-5-carboxylic acid, 2-amino; 2,6-di-t-butyl-4-hydroxymethylene-2,3,5,6-detetrahydrocyclohexanone, phthalic acid, bis(7-methyloctyl) ester and a combination thereof, in the processed sample, and;
 (c) comparing the level of the at least one volatile organic compound from the processed sample with the level of the at least one volatile organic compound in a negative control sample, wherein a significantly different level of the at least one volatile organic compound in the processed sample as compared to the level of the compound in the negative control sample as indicative of the presence of prostate cancer in the subject; and
 (d) creating a volatile organic compound profile score by combining the level of at least one volatile organic compound from the processed sample as indicative of the presence of prostate cancer in the subject, and (ii) administering a prostate cancer therapy to the patient determined to have early prostate cancer.

2. The method of claim 1, wherein sorptive extraction comprising contacting an acidified sample with a polydimethylsiloxane material.

3. The method of claim 2, wherein the polydimethylsiloxane material coats a stir bar.

4. The method of claim 1, wherein determining a level of at least one volatile organic compound associated with prostate cancer comprises performing chemical analysis on a thermal desorption unit (TDU), coupled with gas chromatography and a mass selective detector.

5. The method of claim 1, wherein comparing the level of the at least one volatile organic compound from the processed sample with the level of the at least one volatile organic compound in a negative control sample further comprises normalizing the intensity of the signal against an internal standard, allowing semi-quantitative statistical analysis of VOCs.

6. The method of claim 5, wherein the internal standard is mirex (CAS Number 2385-85-5).

* * * * *